US009700212B2

(12) United States Patent
Takamatsu et al.

(10) Patent No.: US 9,700,212 B2
(45) Date of Patent: Jul. 11, 2017

(54) METHOD FOR NERVE DETECTION BY RAMAN SCATTERING SPECTROSCOPY

(71) Applicant: KYOTO PREFECTURAL PUBLIC UNIVERSITY CORPORATION, Kyoto (JP)

(72) Inventors: Tetsuro Takamatsu, Kyoto (JP); Takeo Minamikawa, Kyoto (JP); Yoshinori Harada, Kyoto (JP)

(73) Assignee: KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 50 days.

(21) Appl. No.: 14/388,035

(22) PCT Filed: Mar. 26, 2013

(86) PCT No.: PCT/JP2013/058775
§ 371 (c)(1),
(2) Date: Sep. 25, 2014

(87) PCT Pub. No.: WO2013/146779
PCT Pub. Date: Oct. 3, 2013

(65) Prior Publication Data
US 2015/0297087 A1 Oct. 22, 2015

(30) Foreign Application Priority Data
Mar. 30, 2012 (JP) ................. 2012-079742

(51) Int. Cl.
*A61B 5/00* (2006.01)
*G01N 21/65* (2006.01)
(52) U.S. Cl.
CPC .............. *A61B 5/0075* (2013.01); *A61B 5/40* (2013.01); *A61B 5/742* (2013.01); *G01N 21/65* (2013.01)

(58) Field of Classification Search
CPC ......... A61B 5/0075; A61B 5/40; A61B 5/742; G01N 21/65
(Continued)

(56) References Cited

U.S. PATENT DOCUMENTS

| 2008/0249380 | A1* | 10/2008 | Van Beek ............ A61B 5/0059 600/310 |
| 2012/0046555 | A1 | 2/2012 | Takamatsu et al. |
| 2014/0118733 | A1* | 5/2014 | Harward ................ G01N 21/65 356/301 |

FOREIGN PATENT DOCUMENTS

| JP | 2000-055809 | 2/2000 |
| JP | 2007-108154 | 4/2007 |

(Continued)

OTHER PUBLICATIONS

Beljebbar et al., "Ex vivo and in vivo diagnosis of C6 glioblastoma development by Raman spectroscopy coupled to a microprobe", Anal. Bioanal. Chem., 398(1): 477-487 (2010).
(Continued)

*Primary Examiner* — Abdullahi Nur
(74) *Attorney, Agent, or Firm* — Wenderoth, Lind & Ponack, L.L.P.

(57) ABSTRACT

The present invention provides a method of detecting nerves, including: step 1 of irradiating a sample with excitation light; step 2 of detecting Raman scattering light from the sample; step 3 of calculating an intensity ratio of a wave number within a specific range of the Raman scattering light detected in the step 2 or extracting a feature of the intensity ratio and subjecting the feature to multivariate analysis and/or statistical analysis; and step 4 of specifically displaying nerves containing unmyelinated nerves, using as an index the intensity ratio or a result from the multivariate analysis and/or the statistical analysis.

7 Claims, 21 Drawing Sheets

(58) Field of Classification Search
USPC .............................................. 356/301, 72–73
See application file for complete search history.

(56) References Cited

FOREIGN PATENT DOCUMENTS

| JP | 2007-147350 | 6/2007 |
|---|---|---|
| WO | 2010/103661 | 9/2010 |

OTHER PUBLICATIONS

Meyer et al., "Nonlinear microscopy, infrared, and Raman microspectroscopy for brain tumor analysis", Journal of Biomedical Optics, 16(2): 021113-1-02113-10 (2011).

Pézolet et al., "Raman Spectroscopy of Nerve Fibers. A Study of Membrane Lipids Under Steady State Conditions", Biophysical Journal, 47(3); 367-372 (1985).

Extended European Search Report issued Dec. 4, 2015, in corresponding application No. 13768225.8.

Minamikawa, T. et al., Label-free Detection of Nerve Tissues by Spontaneous Raman Microspectroscopy, The 51st Annual Conference of Japanese Society for Medical and Biological Engineering Program Ronbunshu (CD-ROM), 2012, No. 02-04-08.

Haka, A. et al., In vivo Margin Assessment during Partial Mastectomy Breast Surgery Using Raman Spectroscopy, Cancer Research, 2006, vol. 66, No. 6, pp. 3317-3322.

Motz, J. et al., In vivo Raman Spectral Pathology of Human Atherosclerosis and Vulnerable Plaque, Journal of Biomedical Optics, 2006, vol. 11, No. 2, 021003.

Torres Filho, I. et al., Measurement of Hemoglobin Oxygen Saturation using Raman Microspectroscopy and 532-nm Excitation, Journal of Applied Physiology, 2008, vol. 104, pp. 1809-1817.

International Search Report for PCT/JP2013/058775, dated Apr. 23, 2013.

Communication Pursuant to Article 94(3) EPC issued Mar. 6, 2017 in corresponding European Application No. 13768225.8.

Huff et al., "Epi-detected Coherent anti-Stokes Raman Scattering Imaging of Deep Tissues in vivo", Proc. of SPIE, 6442:64420E-1-64420E-9 (2007).

* cited by examiner

FIG. 4
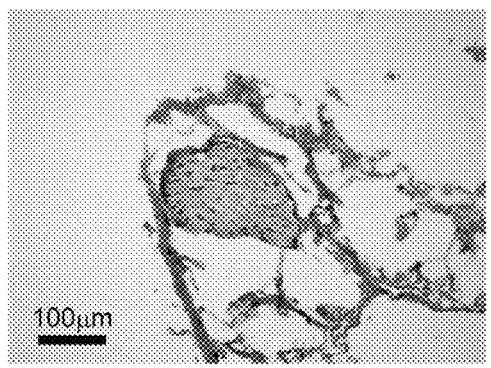
FIG. 5
 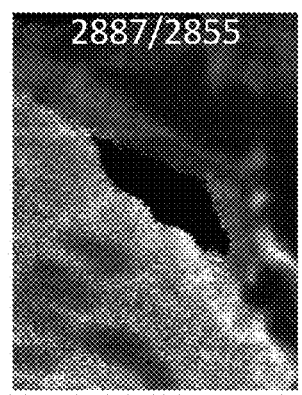 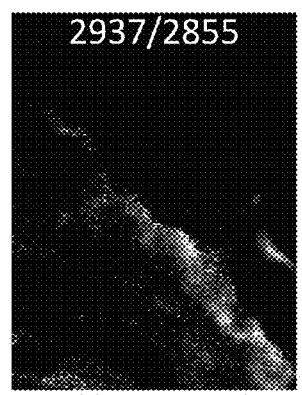
FAT
TISSUE
UNMYELINATED
NERVE
FIBROUS
CONNECTIVE
TISSUE FIG. 6
 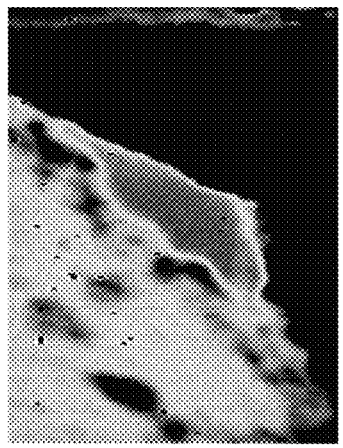 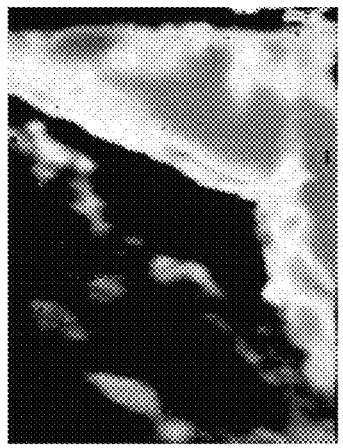
FAT TISSUE · UNMYELINATED NERVE · FIBROUS CONNECTIVE TISSUE FIG. 9
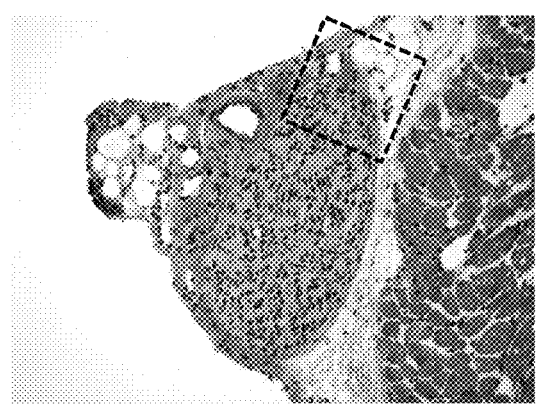
HE stain
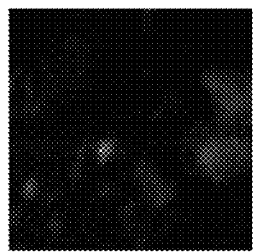
MYELINATED NERVE
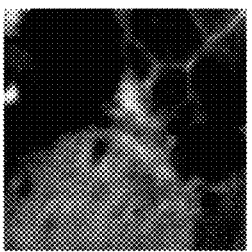
UNMYELINATED NERVE
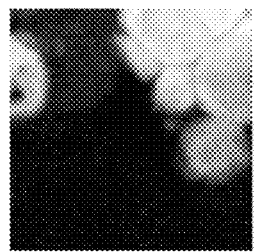
FAT TISSUE
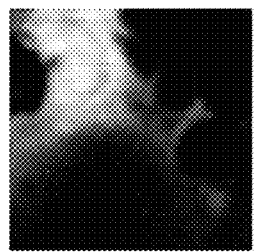
FIBROUS CONNECTIVE TISSUE FIG. 10
HE stain
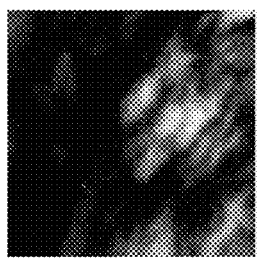
MYELINATED NERVE
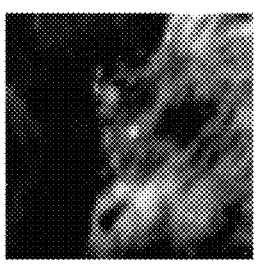
UNMYELINATED NERVE
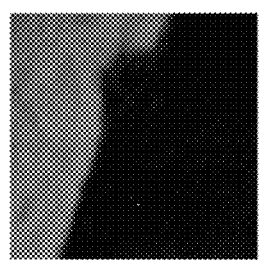
FAT TISSUE
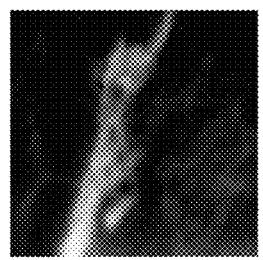
FIBROUS CONNECTIVE TISSUE

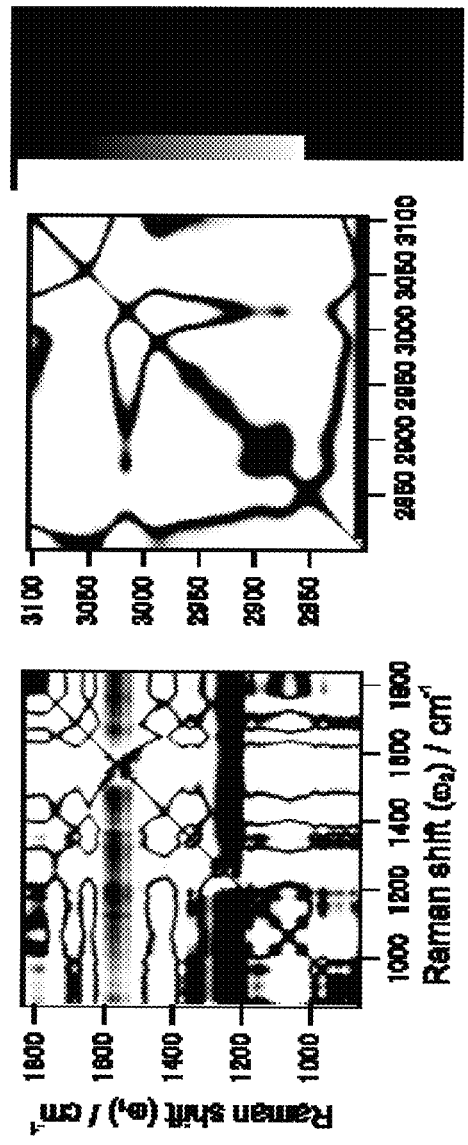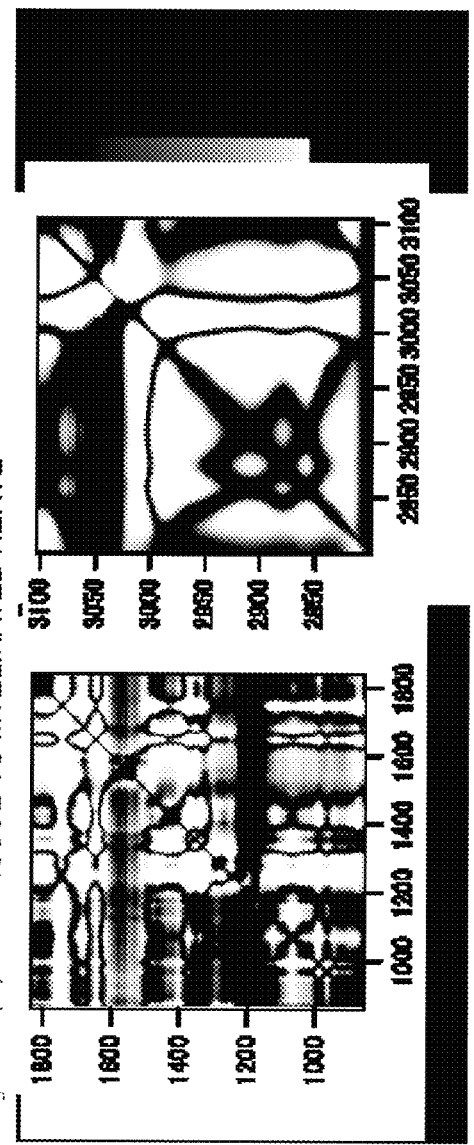

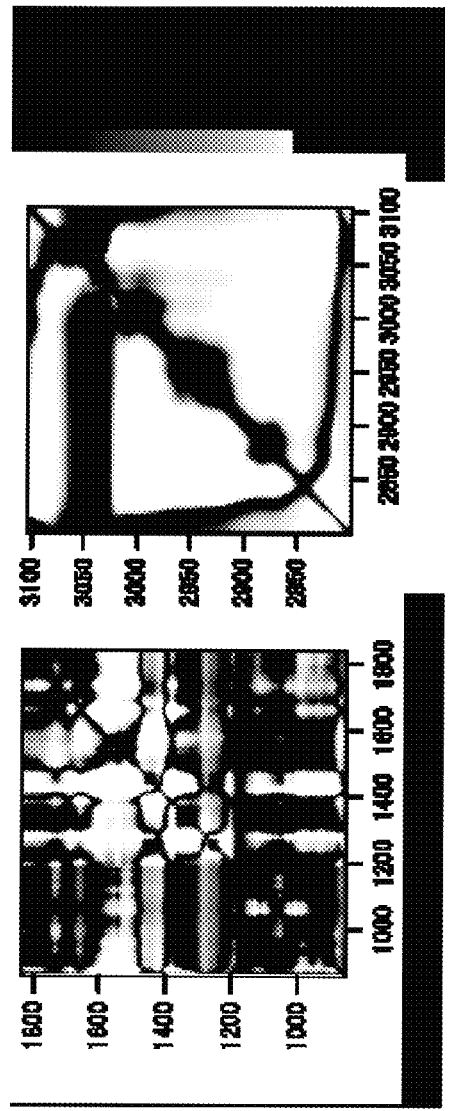
Fig. 12(C) MUSCLE TISSUE VS MYELINATED NERVE
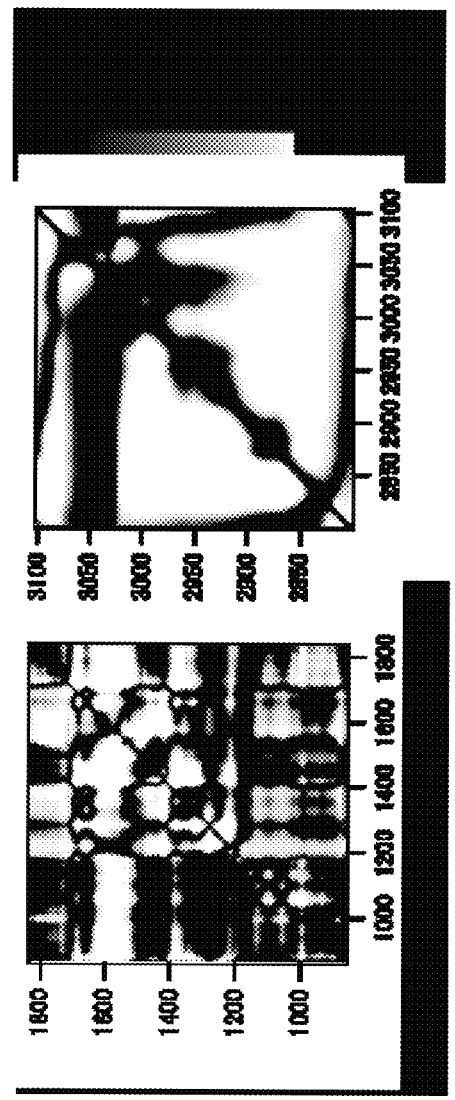
Fig. 12(D) BLOOD VESSEL VS MYELINATED NERVE

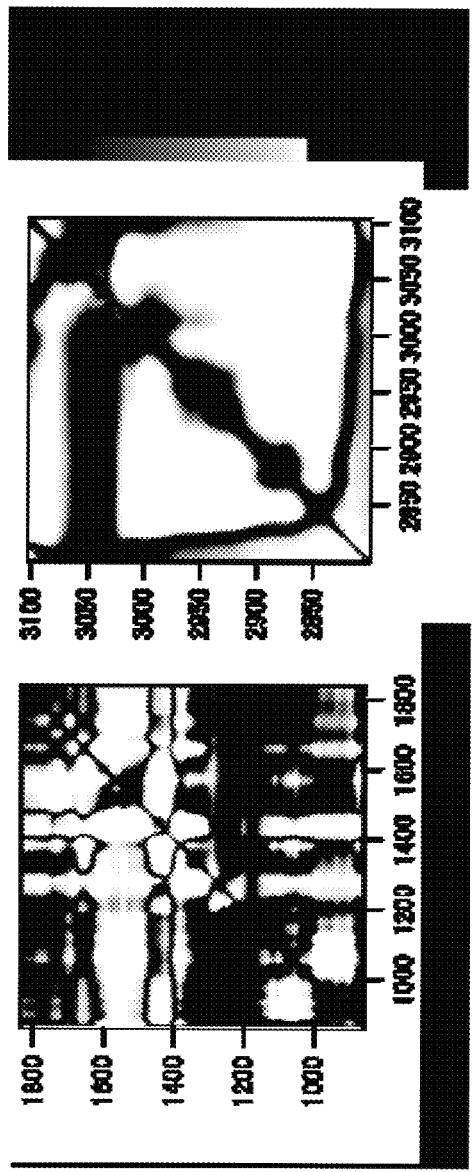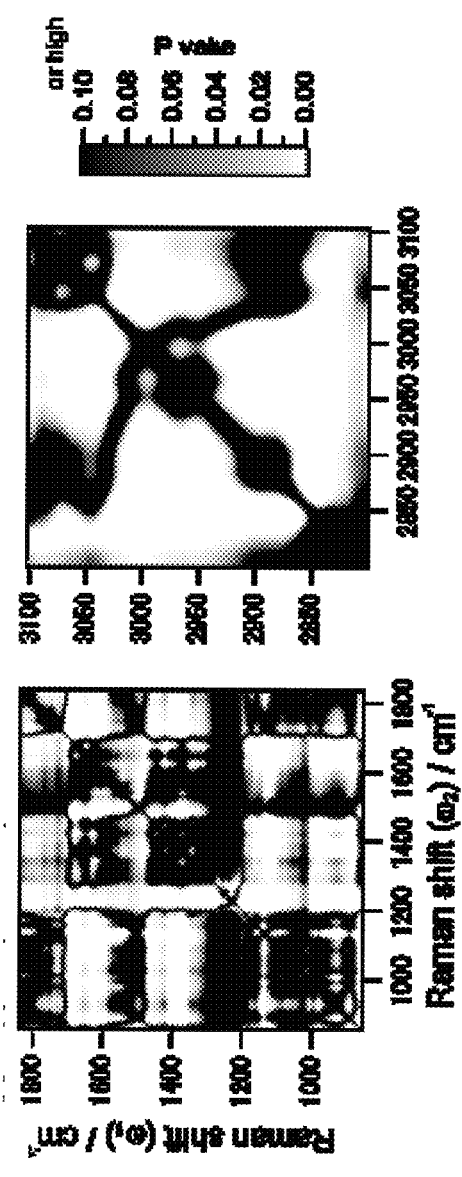
Fig. 12 (E) MYELINATED NERVE AND UNMYELINATED NERVE
Fig. 12 (F) CONNECTIVE TISSUE VS UNMYELINATED NERVE

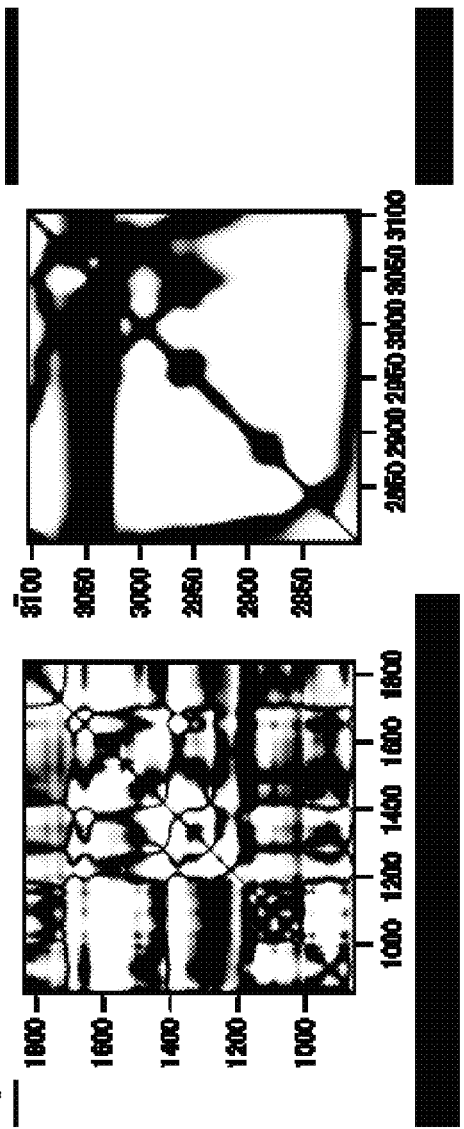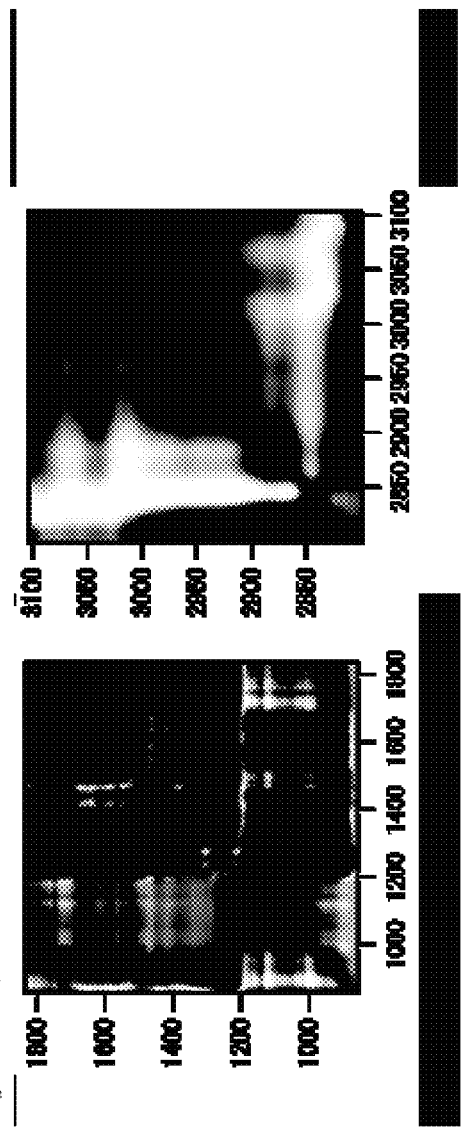

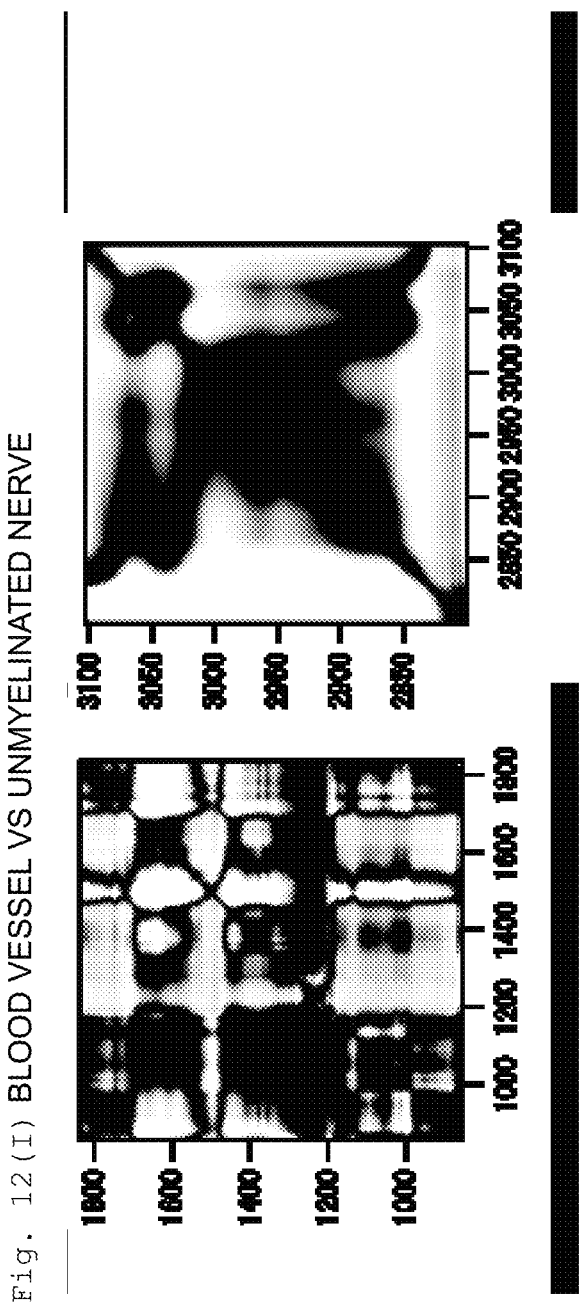
Fig. 12(I) BLOOD VESSEL VS UNMYELINATED NERVE

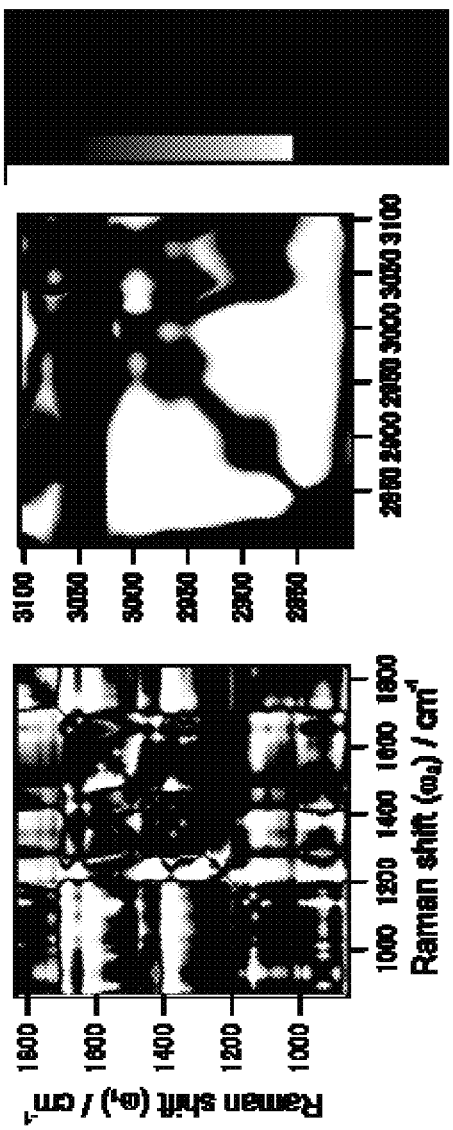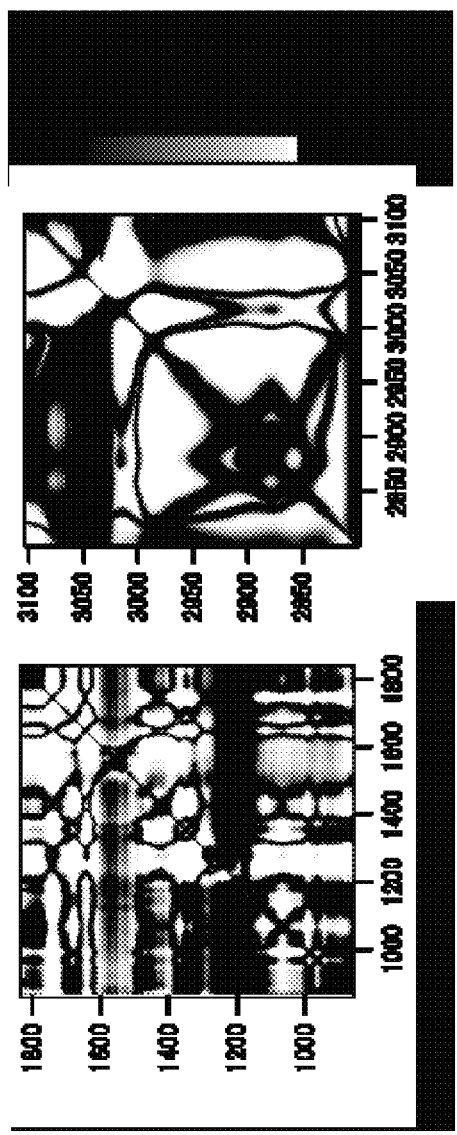

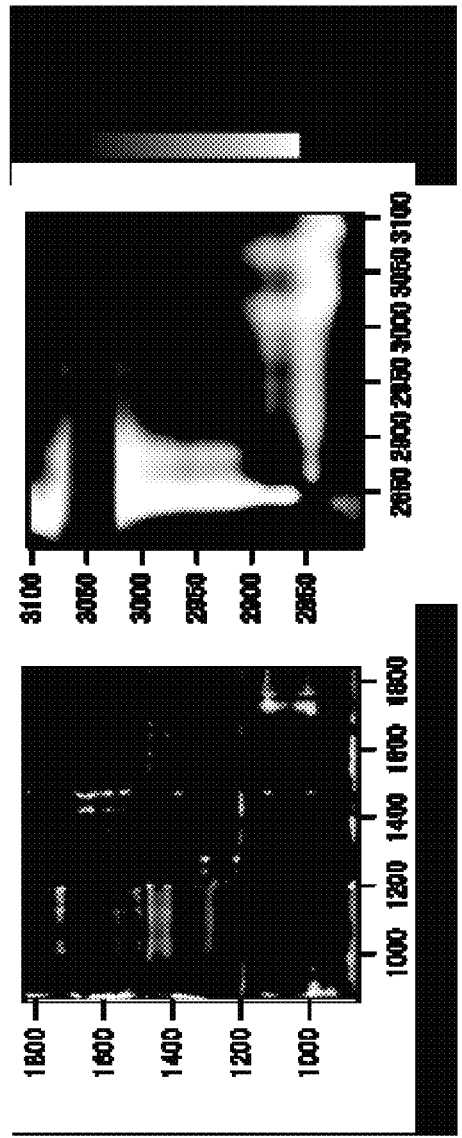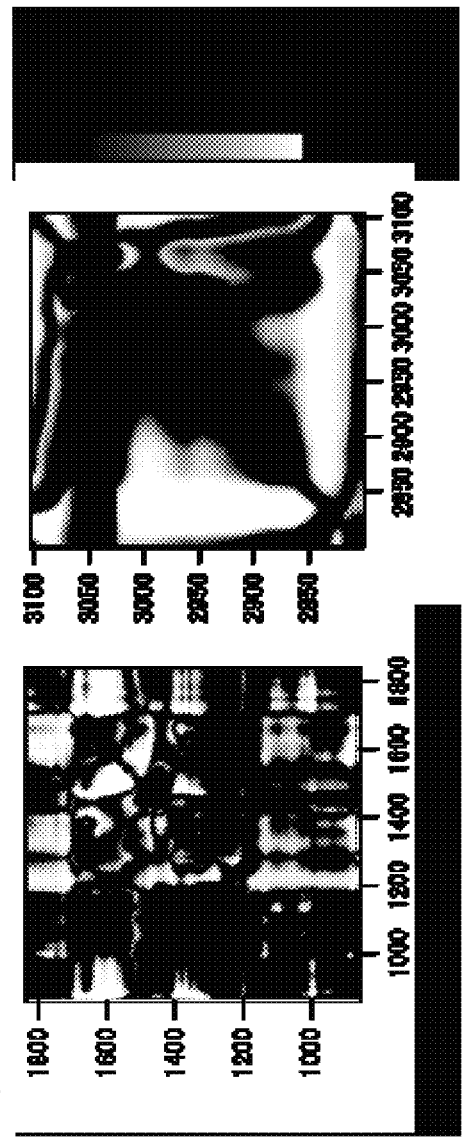

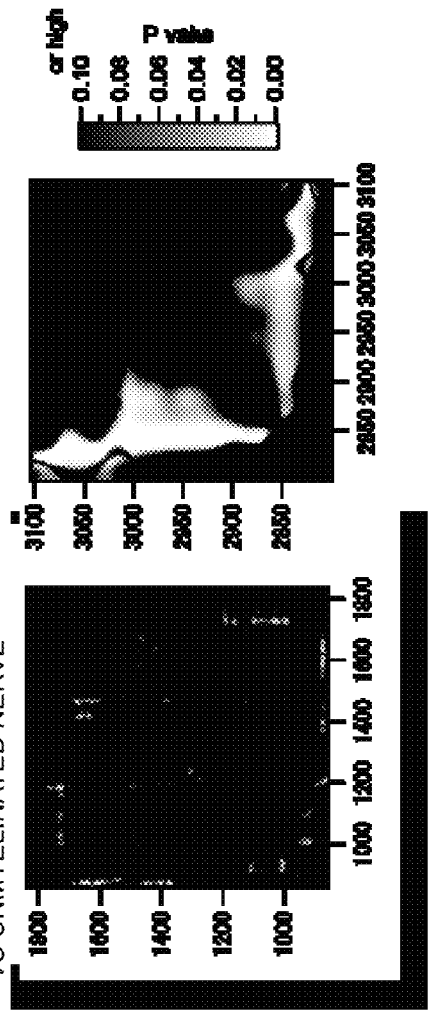
Fig. 13(E) TISSUE (CONTAINING CONNECTIVE TISSUE, FAT TISSUE, MUSCLE TISSUE, AND BLOOD VESSEL) VS UNMYELINATED NERVE
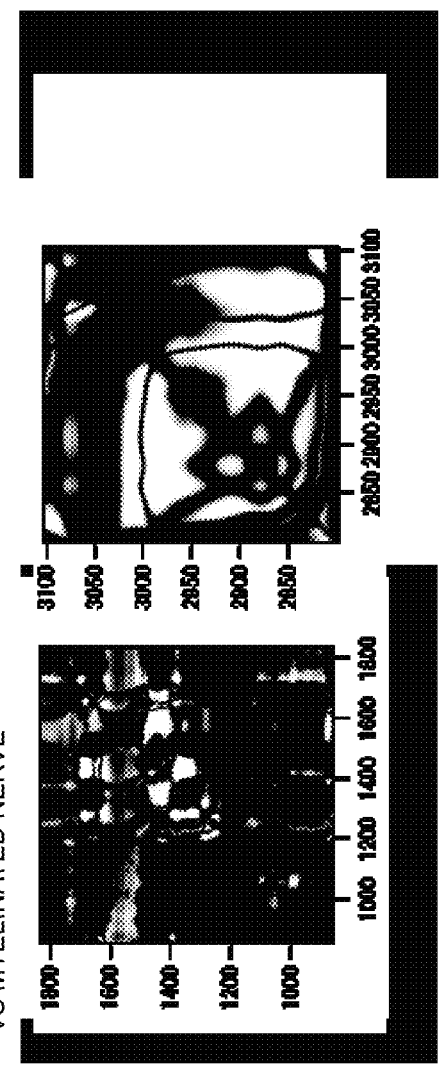
Fig. 13(F) TISSUE (CONTAINING CONNECTIVE TISSUE, FAT TISSUE, MUSCLE TISSUE, AND BLOOD VESSEL) VS MYELINATED NERVE

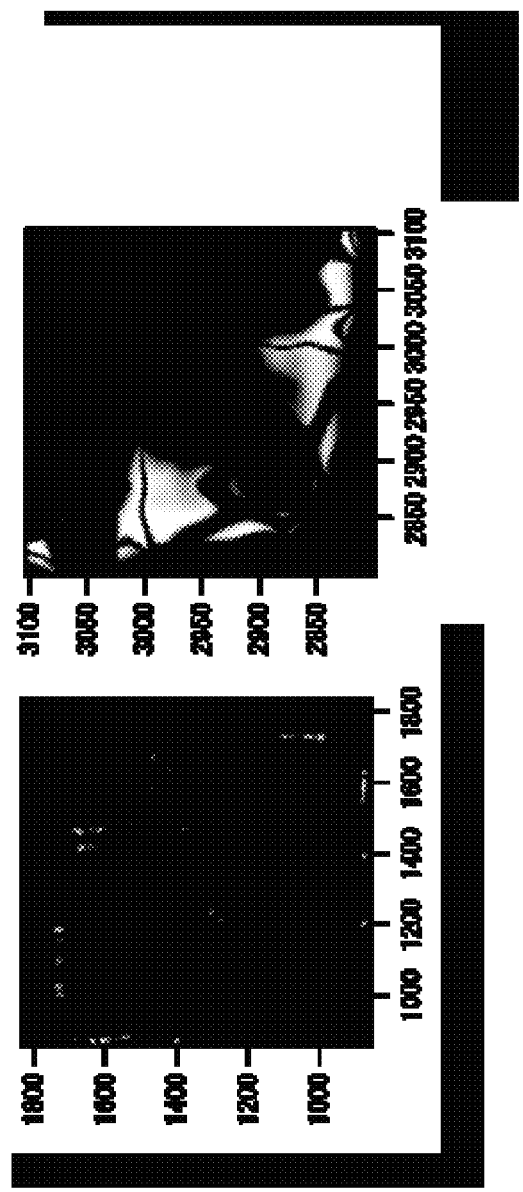
Fig. 13(G) TISSUE (CONTAINING CONNECTIVE TISSUE, FAT TISSUE, MUSCLE TISSUE, AND BLOOD VESSEL) VS MYELINATED NERVE/UNMYELINATED NERVE

METHOD FOR NERVE DETECTION BY RAMAN SCATTERING SPECTROSCOPY

TECHNICAL FIELD

The present invention relates to a method of detecting nerves using Raman scattering spectra from biological tissue. The present invention further relates to a device for detecting nerves using Raman scattering spectra.

BACKGROUND ART

Preserving nerves in operations play important roles in the QOL (quality of life) of patients, as well as preserving organ functions. Hitherto, in order to determine the position of thin nerves, a staining technology using a dye has been improved. However, the staining itself is harmful to humans in most cases, and hence it is difficult to use the staining for observation during operations. Therefore, only thick nerves that can be observed with naked eyes of operators or with white light imaging using an image sensor have been mainly targeted for nerve preservation. There is no technology for determining the position of thin nerves, and hence the determination of the position of nerves has no choice but to depend on the anatomical knowledge, that is, the experience of operators.

Myelinated nerves can still be detected by Raman scattering spectroscopy due to the presence of a myelin sheath rich in lipid. A Raman band derived from lipid (myelin) is to be measured in the myelinated nerves. Therefore, it is difficult to apply this measurement to unmyelinated nerves lacking a myelin sheath, and thus the comprehensive detection of nerves has not been realized.

In contrast, Raman scattering spectroscopy is a form of vibrational spectroscopy. This method provides direct information on specific molecular vibration of chemical bonds in molecules. In Raman scattering spectroscopy, incident light and molecular vibration interact with each other, and thus specific energy changes depending on the molecular vibration can be plotted as a spectrum, thus allowing identification of a substance without staining. Substance detecting methods, imaging methods, and devices that utilize such characteristics of Raman scattering spectroscopy have been developed (Patent Literatures (PTL) 1 and 2). Recent research using Raman scattering spectroscopy in the medical field has focused on tissue diagnosis, such as the diagnosis of cancer (Non-patent Literature (NPL) 1), atherosclerosis (Non-patent Literature (NPL) 2), and oxygen saturation of hemoglobin (Non-patent Literature (NPL) 3). Patent Literature (PTL) 3 discloses a method involving distinguishing and imaging myocardial tissue and blood vessels, and collagen-rich regions. However, none of Non-patent Literatures and Patent Literatures have attempted to detect nerves comprehensively.

CITATION LIST

Patent Literature

PTL 1: Japanese Unexamined Patent Publication No. 2000-55809
PTL 2: Japanese Unexamined Patent Publication No. 2007-147350
PTL 3: WO/2010/103661

Non-patent Literature

NPL 1: Haka, A. S. et al. (2006), Cancer Res. Vol. 66, 3317-22.
NPL 2: Motz, J. T. et al. (2006), J. Biomed. Opt. vol. 11, 021003.
NPL 3: Torres Filho, I. P., et al., (2008), J. Appl. Physiol. 104, 1809-17.

SUMMARY OF INVENTION

Technical Problem

In view of the current situation, an object of the present invention is to detect nerves or to provide a method and a device for detecting nerves.

Solution to Problem

The inventors of the present invention provide the following method and device for detecting nerves.

Item 1. A method of detecting nerves, including:
step 1 of irradiating a sample with excitation light;
step 2 of detecting Raman scattering light from the sample;
step 3 of calculating an intensity ratio of a wave number within a specific range of the Raman scattering light detected in the step 2 or extracting a feature of the intensity ratio and subjecting the feature to multivariate analysis and/or statistical analysis; and
step 4 of specifically displaying nerves containing unmyelinated nerves, using as an index the intensity ratio or a result from the multivariate analysis and/or the statistical analysis.

Item 2. A method of detecting nerves according to Item 1, in which the intensity ratio is one of an intensity ratio between 2,855 $cm^{-1}$ or a peak wave number range of around 2,855 $cm^{-1}$ and 2,933 $cm^{-1}$ or a peak wave number range of around 2,933 $cm^{-1}$ and an intensity ratio between 2,887 $cm^{-1}$ or a peak wave number range of around 2,887 $cm^{-1}$ and 2,933 $cm^{-1}$ or a peak wave number range of around 2,933 $cm^{-1}$.

Item 3. A method of detecting nerves according to Item 2, in which a combination of a numerator and a denominator of the intensity ratio is any one of the following items (i) to (iii):
(i) when the numerator is 2,855 $cm^{-1}$, the denominator is any wave number within a wave number range of from 2,859 $cm^{-1}$ to 3,024 $cm^{-1}$ and 3,068 $cm^{-1}$ to 3,100 $cm^{-1}$;
(ii) when the numerator is 2,887 $cm^{-1}$, the denominator is any wave number within a wave number range of from 2,899 $cm^{-1}$ to 3,024 $cm^{-1}$; and
(iii) when the numerator is 2,933 $cm^{-1}$, the denominator is any wave number within a wave number range of from 2,813 $cm^{-1}$ to 2,912 $cm^{-1}$, 2,940 $cm^{-1}$ to 3,021 $cm^{-1}$, and 3,073 $cm^{-1}$ to 3,089 $cm^{-1}$.

Item 4. A method of detecting nerves according to any one of Items 1 to 3, in which the intensity ratio is an intensity ratio between 2,855 $cm^{-1}$ and 2,933 $cm^{-1}$ or an intensity ratio between 2,887 $cm^{-1}$ and 2,933 $cm^{-1}$.

Item 5. A method of detecting nerves according to any one of Items 1 to 4, in which the sample is a patient undergoing an operation or tissue collected from the patient.

Item 6. A method of detecting nerves according to any one of Items 1 to 5, in which the nerves contain unmyelinated nerves.

Item 7. A device for detecting nerves containing unmyelinated nerves, including:
excitation light irradiation means for irradiating a sample with excitation light;

means for detecting Raman scattering light from the sample;

a spectroscopic portion for dispersing the received Raman scattering light into a spectrum component of each wavelength/wave number;

intensity ratio calculation means for calculating an intensity ratio of a specific wavelength/specific wave number of the Raman scattering light or analyzing means for extracting a feature of the intensity ratio and subjecting the feature to multivariate analysis and/or statistical analysis; and means for specifically displaying nerves containing unmyelinated nerves, using as an index the intensity ratio or a result from the multivariate analysis and/or the statistical analysis.

Item 8. A device for detecting nerves according to Item 7, in which the light source includes a laser light source.

Item 9. A device for detecting nerves according to Item 7 or 8, further including a detector for detecting a Raman spectrum.

Advantageous Effects of Invention

The present invention provides a non-staining optical nerve detection method and device using Raman scattering spectroscopy that employs a light scattering phenomenon caused by molecular vibration. In particular, the present invention provides a non-staining method of detecting nerves containing unmyelinated nerves, which has been impossible hitherto.

The present invention enables nerves containing unmyelinated nerves to be displayed specifically. Thus, the presence and position of nerves can be grasped accurately during an operation through use of the detection method and device of the present invention, and the degradation in QOL after the operation caused by nervous disorder can be suppressed.

BRIEF DESCRIPTION OF DRAWINGS

FIG. 4 shows an HE stained image of gastric branches of vagus nerves.

FIG. 5 shows the detection of unmyelinated nerves, fat tissue, and fibrous connective tissue (tissue including human gastric branches of vagus nerves) based on an intensity ratio.

FIG. 6 shows the detection of unmyelinated nerves, fat tissue, and fibrous connective tissue (tissue including human gastric branches of vagus nerves) by cross-correlation analysis.

FIG. 9 shows the Raman detection of unmyelinated nerves (rat vagus nerves) by a least squares method.

FIG. 10 shows Raman images of nerves including unmyelinated nerves and myelinated nerves (rat celiac plexus) by a least squares method.

FIG. 12 show the detection of nerves based on the intensity ratio of myelinated nerves, unmyelinated nerves, and other tissues. FIG. 12 show p-values obtained by calculating the intensity ratios of (A) connective tissue and myelinated nerves, (B) fat tissue and myelinated nerves, (C) muscle tissue and myelinated nerves, (D) blood vessels and myelinated nerves, (E) myelinated nerves and unmyelinated nerves, (F) connective tissue and unmyelinated nerves, (G) fat tissue and unmyelinated nerves, (H) muscle tissue and unmyelinated nerves, and (I) blood vessels and unmyelinated nerves. A left axis represents a denominator of the intensity ratio, and a lower axis represents a numerator of the intensity ratio.

FIG. 13 show the detection of nerves based on the intensity ratio of nerves (including myelinated nerves and unmyelinated nerves), and other tissues. FIG. 13 show p-values obtained by calculating the intensity ratios of (A) connective tissue and nerves (including myelinated nerves and unmyelinated nerves), (B) fat tissue and nerves (including myelinated nerves and unmyelinated nerves), (C) muscle tissue and nerves (including myelinated nerves and unmyelinated nerves), (D) blood vessels and nerves (including myelinated nerves and unmyelinated nerves), (E) unmyelinated nerves and tissue (including connective tissue, fat tissue, muscle tissue, and blood vessels), (F) myelinated nerves and tissue (including connective tissue, fat tissue, muscle tissue, and blood vessels), and (G) nerves (including myelinated nerves and unmyelinated nerves) and tissue (including connective tissue, fat tissue, muscle tissue, and blood vessels). A left axis represents a denominator of the intensity ratio and a lower axis represents a numerator of the intensity ratio.

DESCRIPTION OF EMBODIMENTS

Figure 1:
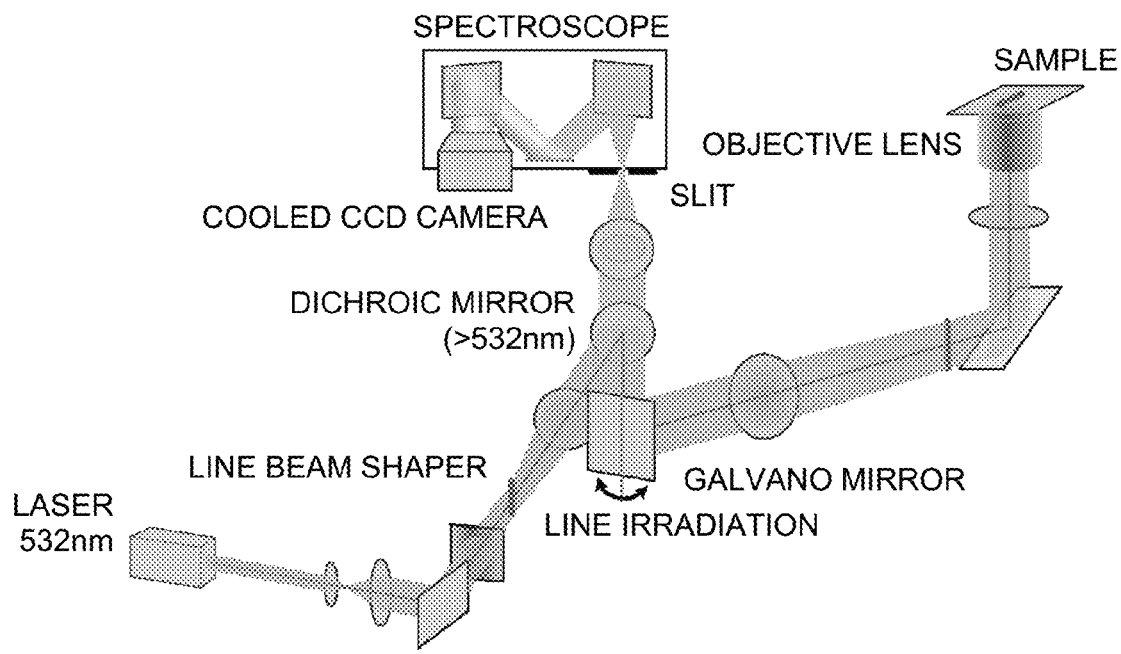
FIG. 1 illustrates a slit-scanning Raman scattering microscope.

The present invention is described below in more detail. However, it should be understood that the scope of the invention is not limited to the specific embodiments described below. Those skilled in the art can easily make various modifications of each element in the embodiments described below, without departing from the spirit of the present invention.

According to one embodiment of the present invention, there is provided a method of detecting nerves, including:
  step 1 of irradiating a sample with excitation light;
  step 2 of detecting Raman scattering light from the sample;

step 3 of calculating an intensity ratio of a wave number within a specific range of the Raman scattering light detected in the step 2 or extracting a feature of the intensity ratio and subjecting the feature to multivariate analysis and/or statistical analysis; and step 4 of specifically displaying nerves containing unmyelinated nerves, using as an index the intensity ratio or a result from the multivariate analysis and/or the statistical analysis.

The phrase "specifically displaying nerves containing unmyelinated nerves" includes both displaying the presence of nerves through use of a sound (warning sound, voice, etc.), light, vibration, heat, or the like, and distinguishing and displaying nerves and perineural tissue through use of a sound (warning sound, voice, etc.), an image, or the like. The perineural tissue includes fat tissue, fibrous connective tissue, muscle tissue, blood vessels, and the like.

In the present invention, first, a sample is irradiated with excitation light. As the sample, there are given animals having nerves, for example, vertebrates, in particular, mammals, or part thereof such as an organ and tissue excised from a living body. Examples of the mammals include humans, monkeys, horses, pigs, cattle, sheep, dogs, cats, rats, and mice, and humans are preferred. An irradiation site of an animal having nerves is not particularly limited as long as the site may have nerves. However, sites in which the damage to nerves during an operation may influence the QOL of a patient are preferably exemplified, and examples thereof include: urinary organs such as the prostate and the bladder; digestive organs such as the rectum, the esophagus, the stomach, the small intestine, the colon, the pancreas, and the liver: nervous organs such as the spinal cord and the brain; the retroperitoneum; the head and neck; the four limbs; or surrounding tissue thereof. In the prostate, bladder, rectum, and the like, the disorder of unmyelinated nerves (parasympathetic nerves) may cause incontinence such as urinary incontinence or fecal incontinence, and hence it is considered to be particularly necessary to prevent a nervous disorder during an operation.

As the application range of the present invention, there is given nerve-sparing surgery for surgery to remove cancer such as nerve-sparing radical prostatectomy and nerve-sparing surgery in rectal cancer, transplantation surgery of various tissues for reconstructing lost tissue after the extirpation of malignant tumor, or microsurgery in plastic surgery such as restoring finger (limb) and emergency surgical operation. The present invention is expected to be useful for identifying nerves that have been overlooked hitherto, and enhance the treatment technology of neuroplasty (neurorrhaphy, nerve transplantation, neurolysis). Further, the present invention can quantitatively determine the presence/absence and quantitative ratio of myelinated nerves/unmyelinated nerves, and hence can also be applied to neurological diagnosis of demyelinating disorder or the like.

As used herein, the nerves include both myelinated nerves and unmyelinated nerves, and the present invention can detect both the myelinated nerves and the unmyelinated nerves. Further, the nerves may be nerve cells or a nerve bundle. In one embodiment, a main target to be detected in the present invention is a nerve bundle. The nerve bundle may be myelinated nerves or unmyelinated nerves, and the myelinated nerves and the unmyelinated nerves may be mixed in various ratios. According to the present invention, in particular, peripheral nerves can be displayed, and needless to say, central nerves can be displayed.

As the wavelength of excitation light, although electromagnetic waves having any wavelengths can be used theoretically, the wavelength is preferably from 350 nm to 1,064 nm, more preferably from 400 nm to 800 nm, still more preferably from 500 nm to 700 nm. A light source to be included in excitation irradiation means can be used without any limit as long as the light source is light-emitting means that is usually used in Raman scattering spectroscopy. Examples of preferred light sources include a 532-nm Nd:YAG laser, a 671-nm DSPP laser, and a 780-nm Ti:S laser. Although, as the excitation light, light from a light source may be directly radiated to a sample, it is preferred that a specific position (for example, a position to be cut by an operation) of a sample be irradiated by an optical fiber.

The Raman scattering light from the sample can be detected by means for detecting Raman scattering light such as a light receiving element. The means for detecting Raman scattering light is not particularly limited in so far as the means can detect Raman scattering light and convert the light into a signal that can be analyzed. The means can be suitably selected from detection means known in this technical field. For example, a light receiving element or an area sensor including light receiving elements arranged in matrix can be used as the means for detecting Raman scattering light. More specifically, a light receiving element such as an avalanche photodiode or a photomultiplier tube, or a two-dimensional CCD or CMOS camera including pixels arranged in an array can be preferably used as the means for detecting Raman scattering light. In a preferred embodiment, Raman scattering light from the sample is passed through a dichroic filter or the like prior to the detection, and is thereby split into excitation light and scattering light (FIG. 1). Further, the split Raman scattering light is spatially dispersed by using a spectroscope including a diffraction grating or a prism based on the wavelength/wave number of the light. The dispersed Raman scattering light is converted into a signal representing a Raman spectrum in the detection means as mentioned above, and is output to analyzing means such as a personal computer.

The means for detecting Raman scattering light detects the intensity of light having each wavelength or wave number in a spectrum of Raman scattering light. The intensity of light of each wavelength/wave number detected with the means for detecting Raman scattering light is detected, and the data is sent to the analyzing means such as a computer to be analyzed. This analysis includes a step of calculating an intensity ratio of a specific wavelength/specific wave number or in a wavelength range/wave number range or a step of extracting a feature of the intensity ratio of the specific wavelength/specific wave number or in the wavelength range/wave number range and subjecting the feature to multivariate analysis and/or statistical analysis, and a step of specifically displaying nerves containing unmyelinated nerves, using as an index the intensity ratio or the result obtained by extracting the feature of the intensity ratio and subjecting the feature to the multivariate analysis and/or the statistical analysis. The analyzed signal is sent to display means (for example, a display in the case of showing the signal with an image, and a loudspeaker or a sound source chip (for example, a sound source such as a CPU) in the case of displaying the signal with a sound such as a voice or a warning sound), nerves containing unmyelinated nerves are specifically detected, and the presence or position of the nerves containing unmyelinated nerves can be grasped. As needed, space information can also be obtained and formed into an image. The position of nerves can be displayed on the display means together with the position of an instrument such as a surgical knife during an operation so that the operation can be performed without damaging the nerves.

Alternatively, an operator can be notified of the presence of nerves with a voice or a warning sound. It is sufficient that the operator recognize the presence of nerves only in the case where nerves are present, and hence the presence of nerves may be "displayed" with an image, a voice/sound, light, vibration, or the like.

The present invention has a feature of detecting the intensity of light within a wave number range of from 0 $cm^{-1}$ to 4,000 $cm^{-1}$ in the Raman scattering light from the sample. The wave number for measuring light intensity is preferably 2,855 $cm^{-1}$, 2,887 $cm^{-1}$, and 2,933 $cm^{-1}$. The nerves containing unmyelinated nerves can be specifically displayed by comparing the wave number intensities of those three wave numbers/wave number ranges. In the case of the unmyelinated nerves, there is no difference in component having a characteristic Raman spectrum such as myelin of the myelinated nerves in the nerves and the surrounding tissue, and hence it has been considered to be difficult to specifically display the unmyelinated nerves. However, the inventors of the present invention have succeeded for the first time in specifically displaying the nerves and the surrounding tissue with an image, a voice/sound, or the like by calculating the intensity ratio of the specific wave number/specific wavelength.

Note that, it is mainly described herein that the intensities are compared in a wave number or a wave number range of Raman scattering light, but the wavelength corresponding to the Raman scattering light can also be used.

Regarding the intensity ratio for detecting nerves, it is sufficient that a specific wavelength/specific wave number or a wavelength range/wave number range in which a significant difference (for example, P<0.05) is obtained regarding an intensity ratio as shown in FIGS. 12 and 13 be designated. For example, in the case where a significant level is set to P<0.05, and a numerator of an intensity ratio (lower axis in the figure) is set to, for example, 2, 855 $cm^{-1}$ in distinguishing the myelinated nerves from the connective tissue, nerves can be detected by designating a denominator (left axis in the figure) of the intensity ratio to a specific wave number or a wave number range of from 2,859 $cm^{-1}$ to 3,024 $cm^{-1}$ and from 3,068 $cm^{-1}$ to 3,100 $cm^{-1}$ as shown in FIG. 12(A). In the case of setting the nominator of the intensity ratio to 2,887 $cm^{-1}$, nerves can be detected by designating a specific wave number or a wave number range of from 2,899 $cm^{-1}$ to 3,024 $cm^{-1}$, and in the case of setting the nominator of the intensity ratio to 2,933 $cm^{-1}$, nerves can be detected by designating a specific wave number or a wave number range of from 2,813 $cm^{-1}$ to 2,912 $cm^{-1}$, from 2,940 $cm^{-1}$ to 3,021 $cm^{-1}$, and from 3,073 $cm^{-1}$ to 3,089 $cm^{-1}$. Further, the same also applies to the case where the nominator of the intensity ratio is set to other specific wave numbers or wave number ranges.

Further, for detecting nerves (including myelinated nerves and unmyelinated nerves) in tissue (including fibrous connective tissue, fat tissue, muscle tissue, and blood vessels), in the case where the nominator (lower axis in the figure) of the intensity ratio is set to, for example, 2,850 $cm^{-1}$, the specific wave number or wave number range of from 2,948 $cm^{-1}$ to 2,999 $cm^{-1}$ or from 3,005 $cm^{-1}$ to 3,022 $cm^{-1}$ can be designated as shown in FIG. 13(G). The same also applies to the case where the nominator of the intensity ratio is designated to other specific wave numbers or wave number ranges.

Further, it is preferred to apply a background removal method, a noise filtering method, or the like, as needed, to the calculation of an intensity ratio. For example, the Raman scattering light is superimposed on autofluorescence from tissue, and hence it is preferred to obtain autofluorescence in advance and to subtract the autofluorescence from a Raman scattering spectrum obtained from a sample. Alternatively, an autofluorescence component may be estimated by a polynomial equation and subtracted as disclosed in Non-patent Literature (Lieber, C.A.; Mahadevan-Jansen, A., Automated Method for Subtraction of Fluorescence from Biological Raman Spectra. Appl. Spectrosc. 2003, 57(11), 1363-1367.). In the noise filtering method, it is preferred to use, for example, a median filter technique, singular value decomposition, a moving-average method, a Kalman filter technique, a Savitzky-Golay method, or the like.

Further, nerves can also be detected from the shape of a Raman spectrum. For example, multivariate analysis such as principal component analysis, a least squares method, or a partial least squares method, and statistical analysis such as cross-correlation analysis of a Raman spectrum can be used.

The principal component analysis and the partial least squares method are each one of a multivariate analysis technique that creates synthesis variables (called principal components) from a plurality of observed variables as a way of concentrating all the observed spectral information. Accordingly, in Raman spectral analysis, the principal component analysis and the partial least squares method can be used for the purpose of extracting spectral features that are unique to several components of the sample from a plurality of Raman spectra obtained from the measurement target. The principal component calculation principle includes the following steps: (1) all the variables are normalized; (2) the axis of each principal component is set so as to maximize the dispersion value of the principal component and thus minimize information loss, and eliminate the correlation among principal components; (3) the principal components are classified as a "first principal component", a "second principal component", and a "third principal component" in descending order according to the degree of dispersion determined; and (4) a weighting factor corresponding to the axis of each principal component is calculated by the least squares method. Individual Raman spectrum scores (principal component scores) relative to the thus obtained principal component spectra are calculated, and nerves are detected based on those values. In this case, the principal component spectra may be calculated from the plurality of Raman spectra obtained from the measurement target, or principal component spectra calculated through use of Raman spectra obtained from nerve tissue or other tissues measured in advance may be used. Further, the detection of nerves may be determined based on one principal component score or based on a ratio of a plurality of scores. Further, the principal component spectra may be designated by a user-defined function in advance, and a principal component score may be calculated through use of the least squares method that is one kind of the multivariate analysis.

In the cross-correlation analysis, components of a sample are estimated by designating a user-defined function in advance and calculating a cross-correlation between the user-defined function and the measured Raman spectrum. In this case, in the user-defined function, a Raman spectrum obtained by the multivariate analysis such as the principal component analysis and the partial least squares method may be used, or a Raman spectrum obtained from the sample may be used. Alternatively, any Raman spectrum may be designated.

The presence/absence of nerves may be determined based on only one intensity ratio or only one result from the multivariate analysis and/or statistical analysis, or the presence/absence of nerves may be determined based on a combination of two or more intensity ratios or two or more results from the multivariate analysis and/or statistical analysis. The display means may determine the presence of nerves in the case where even one intensity ratio of a Raman scattering light spectrum from a sample or even one result from the multivariate analysis and/or statistical analysis falls within a predetermined range, or the display means may determine the presence of nerves in the case where two or more intensity ratios or two or more results from the multivariate analysis and/or statistical analysis fall within the predetermined range.

A signal of a site determined to be nerves by the intensity ratio calculation means or the analyzing means and a signal of a site determined to be non-nerves by the intensity ratio calculation means or the analyzing means are sent to a display device such as a display, a sound source, a light source, a vibration source, or the like, and the presence/absence of nerves is displayed. Further, the nerves can be displayed as an image in the display device. The display and imaging of the nerves and the other tissues can be performed by a personal computer or the like using software known in this technical field. For example, MATLAB (Mathworks) can be used for display.

Figure 2:
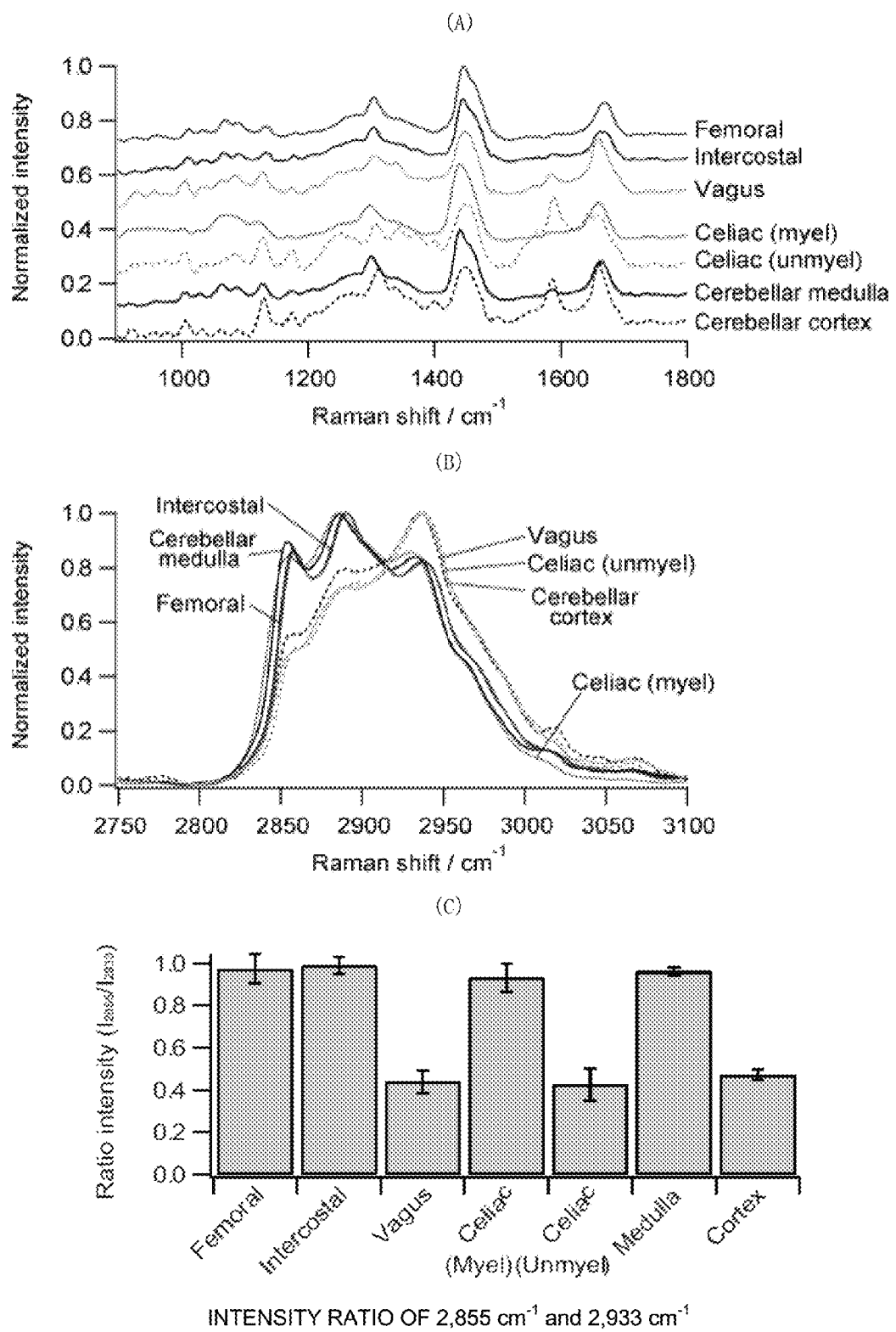
FIG. 2 show Raman spectra of various nerves. The nerves include intercostal nerves (myelinated nerves), vagus nerves (unmyelinated nerves), celiac nerves (myelinated nerves), celiac nerves (unmyelinated nerves), femoral nerves (myelinated nerves), cerebellar medulla (myelinated nerves), and cerebellar cortex (unmyelinated nerves).
Figure 3:
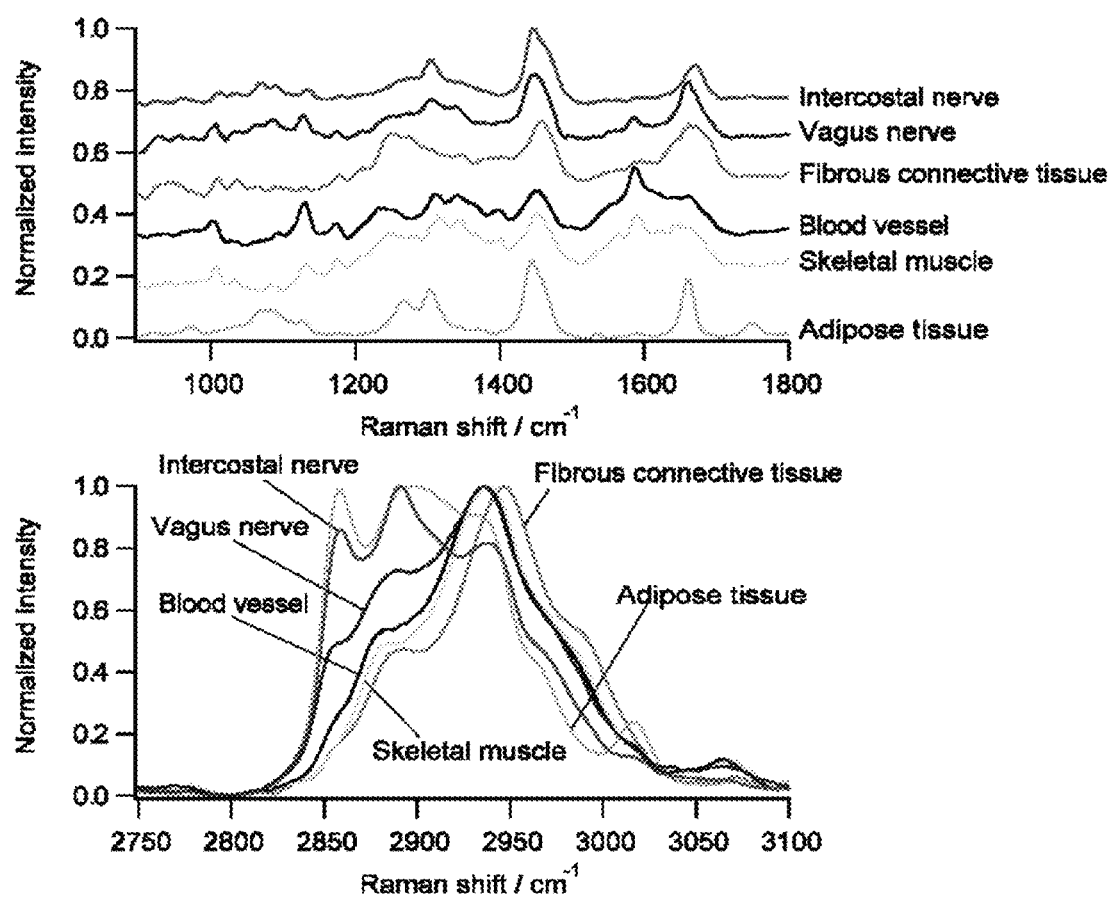
FIG. 3 shows Raman spectra of various tissues. The Raman spectra of the tissues exhibit characteristic spectra derived from molecules forming each tissue. Nerve tissue is differentiated based on the difference in spectrum. The tissues include intercostal nerves, vagus nerves, fibrous connective tissue, blood vessels (media), muscle tissue, and fat tissue.

FIGS. 2 and 3 show an example of Raman spectra that are characteristic of nerve cells.

The above-described series of steps, including irradiation of a sample with excitation light, detection of Raman scattering light from the sample, conversion of the detected Raman scattering light into a Raman spectrum signal, and display/imaging of a Raman spectrum, can be carried out, for example, by the method described in Japanese Unexamined Patent Publication No. 2007-147357 and/or using a commercially available Raman spectroscopic detecting device (such as a Raman microscope manufactured by Nanophoton Corporation).

It is preferred that both the excitation light irradiation means and the Raman scattering light detection means of the device of the present invention have a configuration capable of radiating laser light from a tip end of an elongated arm such as an optical fiber and receiving (detecting) Raman scattering light, from the viewpoint of irradiating the vicinity (sample) of a site to be extirpated/excised during a surgical operation with excitation light (preferably laser light) and detecting Raman scattering light from the irradiated site of the sample.

In another preferred embodiment, the present invention relates to a device for detecting nerves containing unmyelinated nerves, including: excitation light irradiation means (including a light source) for irradiating a sample with excitation light; a spectroscope for dispersing Raman scattering light received from the sample into a spectrum component of each wavelength/wave number; Raman scattering light detection means for detecting the Raman scattering light (in particular, Raman scattering light dispersed into each wavelength/wave number by the spectroscope) from the sample; intensity ratio calculation means for calculating an intensity ratio of a specific wavelength/specific wave number or a wavelength range/wave number range of the Raman scattering light or means for extracting a feature of the intensity ratio of the specific wavelength/specific wave number or the wavelength range/wave number range of the Raman scattering light and subjecting the feature to multivariate analysis and/or statistical analysis, means for specifically displaying nerves containing unmyelinated nerves, using the intensity ratio as an index; and means for imaging the nerves as needed.

As used herein, it is sufficient that the Raman scattering spectroscopy be spectroscopy capable of obtaining a Raman spectrum, and examples thereof include spontaneous Raman scattering spectroscopy, time-resolved Raman scattering spectroscopy, and non-linear Raman scattering spectroscopy. Examples of the non-linear Raman scattering spectroscopy include coherent anti-stokes Raman scattering spectroscopy and stimulated Raman scattering spectroscopy.

The Raman scattering light detection means receives information on the intensity at each position and each wave number (wavelength) of Raman scattering light reflected from a sample and sends the signal to the analyzing means. The Raman scattering light from the sample may be sent directly to the Raman scattering light detection means, but it is preferred that the Raman scattering light be sent to the Raman scattering light detection means through the spectroscopic portion so that the Raman scattering light detection means can detect each wave number (wavelength) of a Raman spectrum and an intensity thereof easily. Examples of the Raman scattering light detection means or the detector for detecting a Raman spectrum include a light receiving element such as a photomultiplier tube, a CCD camera such as a cooled CCD camera, a CMOS camera, a photodiode array, a photodiode, and a PMT. The CCD camera is preferred.

The information on the Raman scattering light from the sample, which is detected by the Raman scattering light detection means, is sent to the intensity ratio calculation means such as a computer or the means for extracting a feature of the intensity ratio and subjecting the feature to multivariate analysis and/or statistical analysis, and thus the information is used for calculating the intensity ratio at each position of the sample or subjected to the multivariate analysis and/or the statistical analysis. Next, the intensity ratio at each position of the sample is calculated or a feature of the intensity ratio is extracted and subjected to the multivariate analysis and/or the statistical analysis. Then, the intensity ratio or the signal from the multivariate analysis and/or the statistical analysis is sent to the display means. The value of a specific intensity ratio or a portion of the result from the multivariate analysis and/or the statistical analysis is displayed as nerves or the presence of the nerves is displayed, and as needed, a portion having an intensity ratio other than that in a specific range is displayed as non-nerves so that the operator can recognize the presence of the nerves. Examples of the display include the display of an image on a display device, the display with a voice or a sound using a loudspeaker or a sound source (including an electronic sound source such as a CPU), and the display with light, heat, vibration, or the like. In the case of the display of an image, nerves and other tissues can be distinguished and displayed. In the case of the display with a voice/sound, light, heat, vibration, or the like, the nerves may be displayed by generating a larger sound, stronger light, larger vibration, higher heat, or the like as the nerves are present closer to the surface and are thicker. As needed, the nerves are displayed by imaging or with a voice/sound by being matched with the Raman scattering light measurement position. As described in Non-patent Literature (P. Matousek, Deep non-invasive Raman spectroscopy of living tissue and powders, Chem Soc Rev, 36(8), 1292-304 (2007), a deep portion (for example, about 20 mm) can also be detected by shifting an excitation position and a detection position from each other spatially by a spatially offset detection method. Alternatively, the deep portion can also be detected by enhancing the detection sensitivity through application of a noise removal filter, a signal modulation/recovery theory, or the like.

The method and device of the present invention enable nerves (myelinated nerves and unmyelinated nerves) to be detected specifically. The method and device of the present invention can preferably display nerves and the other tissues separately and can also display myelinated nerves, unmyelinated nerves, and the other tissues separately.

The present invention can visualize nerves. The nerves are classified into peripheral nerves and central nerves. The central nerves have a function of serving as a reflex center with respect to stimulus from a periphery and integrating all the nerves, or have a function of memory, emotion, and decision-making. The peripheral nerves connect the central nerves to each organ and tissue, and control movement, sensation, autonomic function, and the like. The central nerves and peripheral nerves are roughly classified into myelinated nerves and unmyelinated nerves. Somatic nerves controlling the perception and movement of a body belong to the myelinated nerves. In autonomic nerves involved in the autonomic control of the internal organs and blood vessels, preganglionic autonomic nerves belong to myelinated nerves, and postganglionic autonomic nerves belong to unmyelinated nerves. In the myelinated nerves, an axon of each nerve cell is covered with a film mainly formed of lipid called a myelin sheath. On the other hand, the unmyelinated nerves are different from the myelinated nerves in that a myelin sheath is not present. Hitherto, the myelinated nerves have been able to be detected by detecting a myelin that is a characteristic component, but the unmyelinated nerves cannot be detected.

The peripheral nerves have a configuration in which some axons gather to form one nerve bundle. The nerve bundle includes myelinated nerves, unmyelinated nerves, minute blood vessels, fibrous connective tissue (collagen, etc.), and the like and is covered with a perineuria. On the periphery of the nerve bundle, perineural tissue such as fat tissue, fibrous connective tissue (collagen, etc.), blood vessels, and muscle tissue is present. The present invention can specifically display the nerve bundle, and hence allows the perineural tissue to be removed without damaging nerves.

The ratio of the myelinated nerves and the unmyelinated nerves present in the nerve bundle greatly varies depending on the site. For example, the intercostal nerves, ischiatic nerves, femoral nerves, and the like are mostly occupied by the myelinated nerves, and the vagus nerves are mostly occupied by the unmyelinated nerves. Nerve bundles close to organs and tissue include those which are mostly occupied by the myelinated nerves, those which are mostly occupied by the unmyelinated nerves, and those in which the myelinated nerves and the unmyelinated nerves are mixed. The present invention can detect both the myelinated nerves and the unmyelinated nerves, and hence can detect both of them irrespective of the ratio of the myelinated nerves and the unmyelinated nerves present in nerve bundles.

These nerve bundles start from the central nervous system including the thoracic cord, lumbus, and sacral cord and extend to each organ and tissue while being branched and joined.

It is important to perform an operation while preserving nerves that are present as a nerve bundle during a surgical operation from the viewpoint of the recovery after the operation and the avoidance of after effects. However, actually, a great number of cases have been reported in which nerves that are present in tissue cannot be preserved, and after effects are caused.

For example, in radical prostatectomy, nerve-sparing surgery is conducted with a neurovascular bundle distinguishable with the naked eyes of an operator being a mark. However, thin surrounding peripheral nerves cannot be preserved in most cases, and urinary continence disorder and erectile dysfunction after operations have been reported. This is because peripheral nerves that cannot be recognized with the naked eyes of an operator or by the observation with a camera are not preserved. The nerves involved in erectile ability and urinary continence extending around the prostate gland include autonomic nerves (unmyelinated nerves) such as hypogastric nerves, pelvic nerves, and cavernous nerves, and somatic nerves (myelinated nerves) such as pudic nerves and dorsal nerves of penis. Therefore, the measurement of only the myelinated nerves is insufficient, and it is necessary to measure both the myelinated nerves and the unmyelinated nerves. These problems are similarly found in nerve-sparing surgery in rectal cancer and nerve-sparing surgery of the other sites.

Further, in plastic surgery, nerve suture of a diameter of 1 mm or less is conducted, and hence microsurgery is conducted in which an operation is performed under a microscope. Examples of the microsurgery include restoring finger, breast reconstruction surgery after mastectomy, reconstruction by tissue transplantation with respect to facial nerve paralysis or the like, penis reconstruction using a forearm flap, and urethral reconstruction by appendix transplantation. However, it is difficult to identify nerves even under a microscope in some cases, and hence a procedure for specifically displaying nerves is required.

Accordingly, there is a demand for a technology of visualizing thin nerves that are difficult to observe with naked eyes of an operator. The nerves include both the myelinated nerves and the unmyelinated nerves in a mixed manner as described above, and it is necessary to measure both of them.

EXAMPLES

The present invention is described below in more detail with reference to Examples. However, it should be understood that the scope of the invention is not limited to the specific examples below.

Example 1

General View of Experimental Device and Experimental Method

FIG. 1 illustrates a general view of an experimental device.

Slit-scanning Raman scattering microscope: RAMAN-11, manufactured by Nanophoton Corporation Cooled CCD camera: Pixis 400 BR, manufactured by Princeton Instruments, −70° C., 1,340×400 pixels Objective lens: UPLSAPO, Manufactured by Olympus Corporation, ×60, NA=1.2

Experimental Method
(1) Tissue Sample
Rat Tissue

A healthy Wistar rat was euthanized by an overdose of an anesthetic, and each tissue was obtained.

Chest tissue containing intercostal nerves, tissue in the vicinity of the esophagus containing vagus nerves, femoral nerves and surrounding tissue thereof, celiac plexus, cerebellum Type: Wister Rat
Age: Young-adult (8-10 weekly age)

Human Tissue

The periprostatic tissue of a patient who has undergone radical prostatectomy was obtained. The tissue containing a vagus nerve gastric branch of a patient who has undergone stomach cancer extirpation was obtained.

(2) Preparation of Sample Section

Each obtained tissue was embedded in Frozen Section Compound (FSC22, Leica), and rapidly frozen with dry ice-acetone. The tissue was stored in a deep freezer at −80° C. until measurement.

The frozen tissue was cut to a section having a thickness of 5 μm. The section was held between a slide glass and a cover glass and measured.

(3) Spectral Analysis

Autofluorescence is superimposed on a Raman spectrum of living tissue. In order to exclude the influence of the autofluorescence, an autofluorescence spectrum is estimated by software for a Raman microscope manufactured by Nanophoton Corporation, and the influence of the autofluorescence was subtracted. Specifically, modified least-squares fifth-order polynomial curve fitting (Lieber Calif., Mahadevan-Jansen A (2003) Automated Method for Subtraction of Fluorescence from Biological Raman Spectra. Appl Spectrosc 57 (11): 1363-1367) was applied and repeated 10 times to estimate an autofluorescence.

Further, a spectroscope was calibrated for wavelength through use of a Raman spectrum of ethanol having a known Raman shift.

Experimental Result

FIG. 2 show Raman spectra of various nerves, and FIG. 3 shows Raman spectra of the nerves and the other tissues.

Next, the detection of nerves using tissue containing unmyelinated nerves (human vagus nerve gastric branch) is described.

FIG. 4 shows an HE stained image of the obtained human vagus nerve gastric branch.

FIG. 5 shows Raman images of unmyelinated nerves and surrounding tissue (fibrous connective tissue) based on an intensity ratio. Imaging of fat tissue can be performed through use of an intensity ratio of 2,855 cm$^{-1}$ and 2,872 cm$^{-1}$. Imaging of unmyelinated nerves can be performed through use of an intensity ratio of 2,887 cm$^{-1}$ and 2,855 cm$^{-1}$. Imaging of fibrous connective tissue can be performed through use of an intensity ratio of 2,937$^{-1}$ and 2,855 cm$^{-1}$.

FIG. 6 shows Raman images of unmyelinated nerves and surrounding tissue (fibrous connective tissue) by cross-correlation analysis. As reference Raman spectra used for the cross-correlation analysis, Raman spectra obtained from unmyelinated nerves, fat tissue, and fibrous connective tissue in advance were used. In the cross-correlation of the fat tissue and the reference Raman spectrum, imaging of the fat tissue can be performed. In the cross-correlation of the unmyelinated nerves and the reference Raman spectrum, imaging of the unmyelinated nerves can be performed. In the cross-correlation of the fibrous connective tissue and the reference Raman spectrum, imaging of the fibrous connective tissue can be performed.

Figure 7:
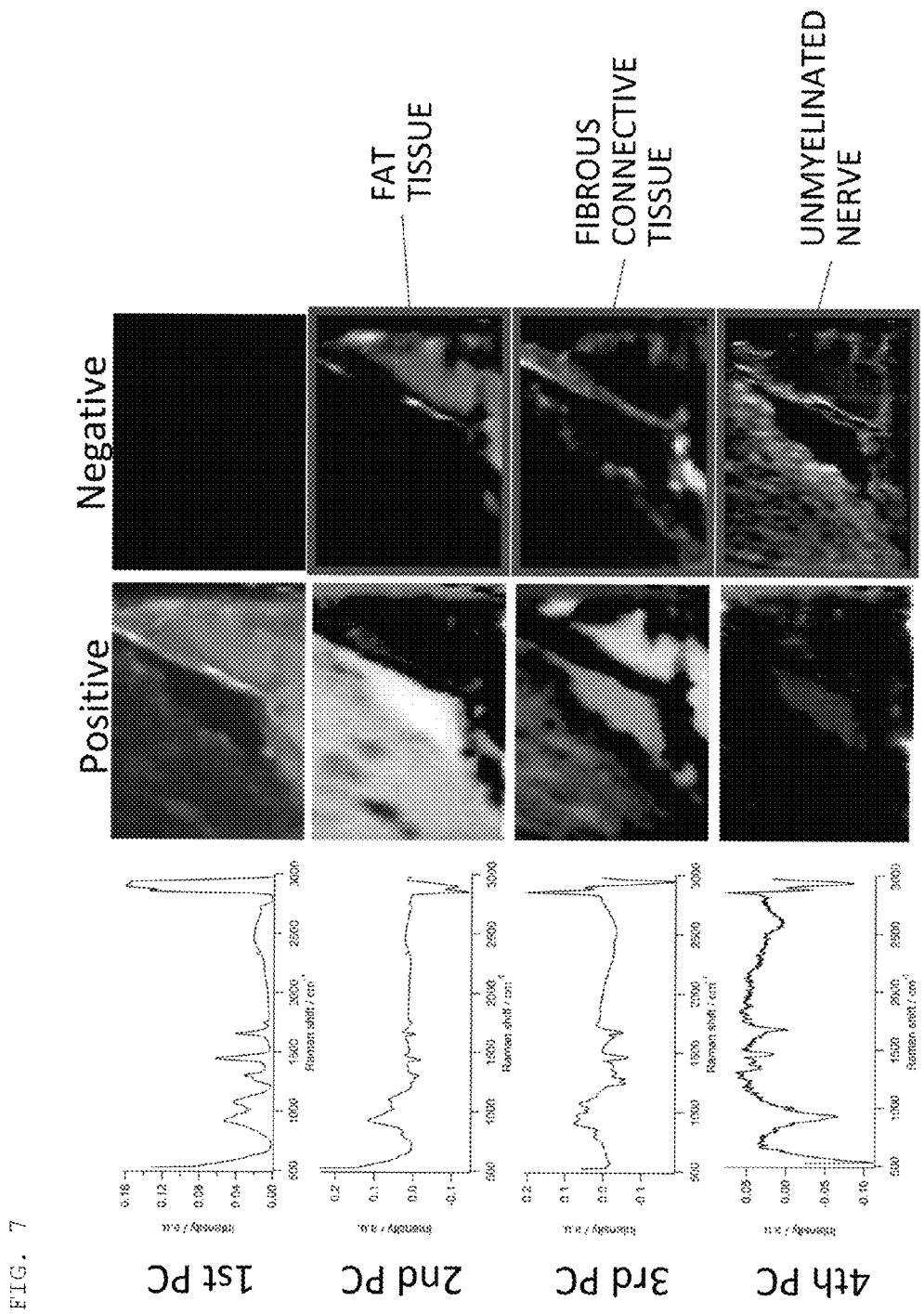
FIG. 7 shows the detection of unmyelinated nerves, fat tissue, and fibrous connective tissue (tissue including human gastric branches of vagus nerves) by principal component analysis.

FIG. 7 shows nerves and detection of nerves by principal component analysis. In the principal component analysis, first, a Raman spectrum at each point in a two-dimensional space was obtained and defined as analysis data. In the subsequent principal component analysis, a first principal component to a fourth principal component were obtained, and a space map of each principal component score was displayed. As a result, the score map of a negative value of the second principal component was matched with the space distribution of the fat tissue, the score map of a negative value of the third principal component was matched with the space distribution of the fibrous connective tissue, and the score map of a negative value of the fourth principal component was matched with the space distribution of the unmyelinated nerves.

Figure 8:
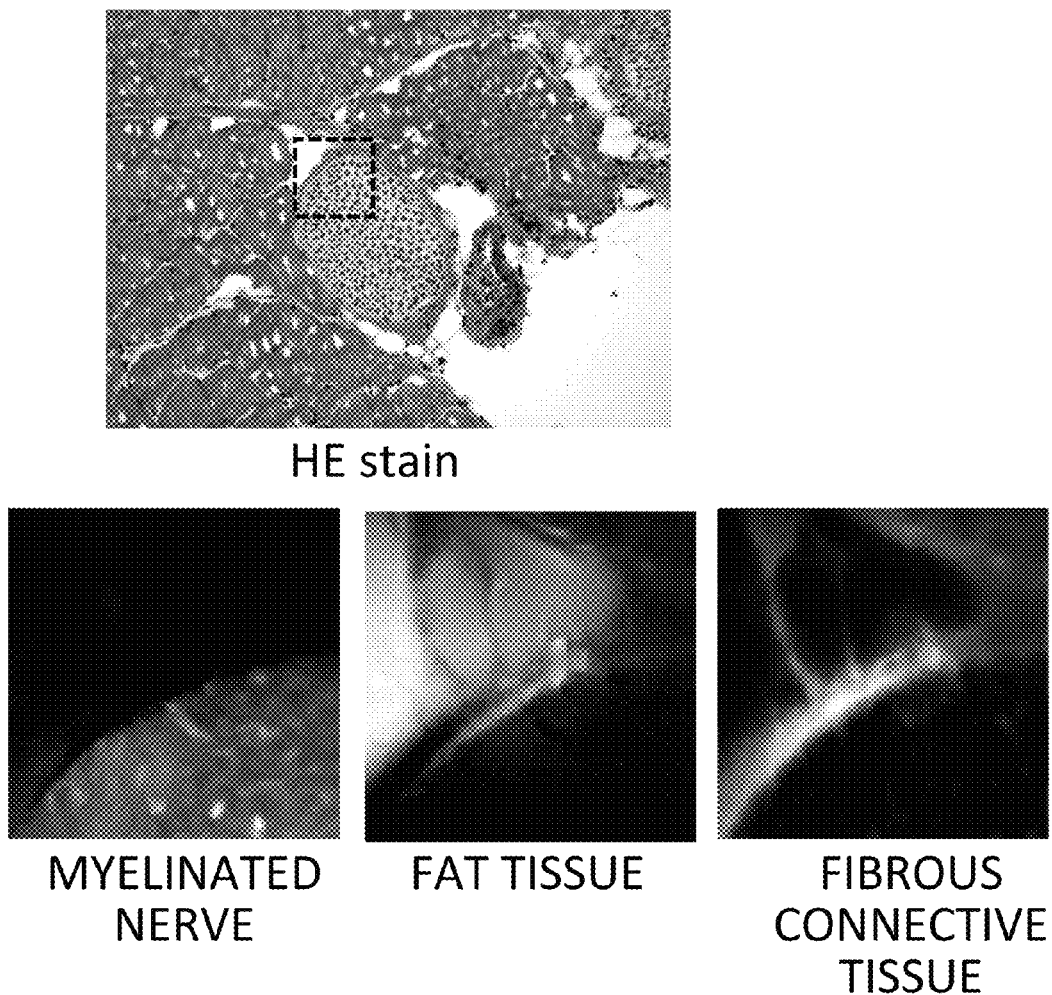
FIG. 8 shows the Raman detection of myelinated nerves (rat intercostal nerves) by a least squares method.
Figure 11:
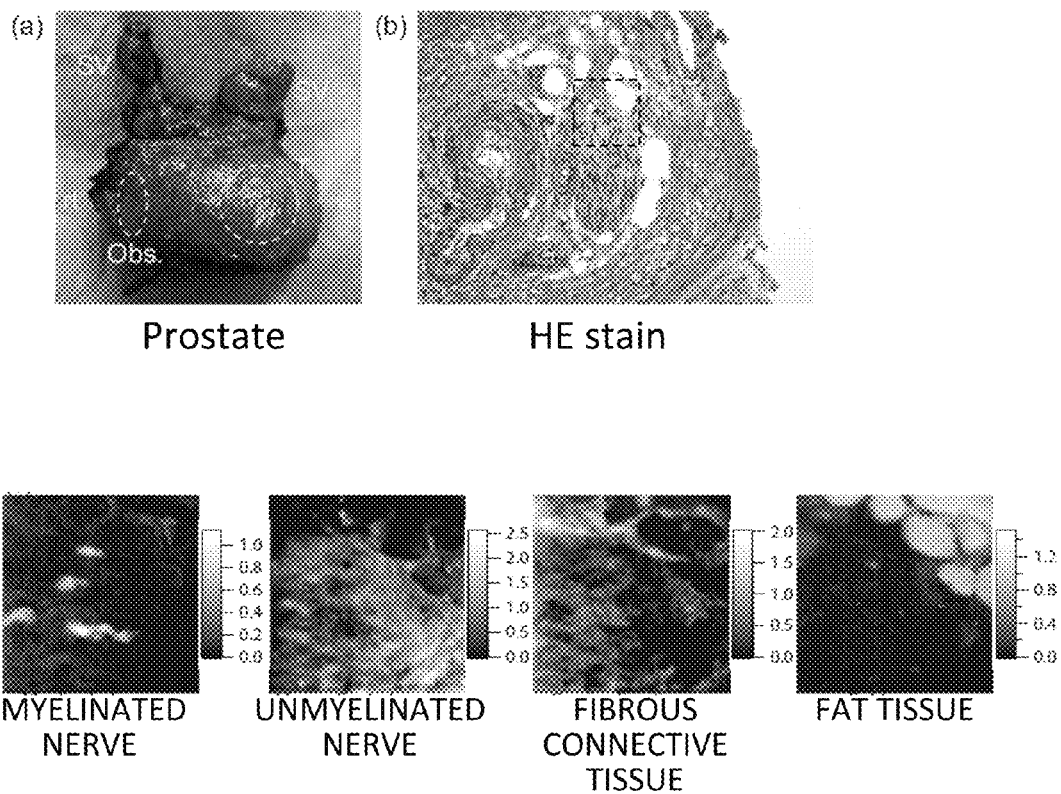
FIG. 11 shows Raman images of nerves including unmyelinated nerves and myelinated nerves (human periprostatic tissue) by a least squares method.

Next, the results obtained by detecting nerves through use of a least squares method are described. FIG. 8 shows myelinated nerves (rat intercostal nerves). FIG. 9 shows unmyelinated nerves (rat vagus nerves). FIG. 10 shows myelinated nerves and unmyelinated nerves (rat celiac plexus). FIG. 11 shows myelinated nerves and unmyelinated nerves (human periprostatic tissue). In the least squares method, a score of each component was calculated in accordance with the following equation.

$$S_i(x,y) = aS_{fat} + bS_{connect} + cS_{myel} + dS_{unmyel}$$ [Math. 1]

Note that, $S_i$, $S_{fat}$, $S_{connect}$, $S_{myel}$, $S_{unmyel}$ represent a Raman spectrum at any point (x, y), a Raman spectrum of the fat tissue, a Raman spectrum of the fibrous connective tissue, a Raman spectrum of the myelinated nerves, and a Raman spectrum of the unmyelinated nerves.

Example 2

Distinguishing Nerves and Surrounding Tissue Thereof Based on Intensity Ratio

Raman spectra of myelinated nerves, unmyelinated nerves, connective tissue, fat tissue, muscle tissue (striated muscle), and blood vessels (media) were obtained, and whether or not there was a significant difference in intensity ratio in each Raman shift was investigated.

Method of Calculating Intensity Ratio $$I_{ratio} = \frac{I_{\omega 2}}{I_{\omega 1}}$$ [Math. 2]

$I_{ratio}$: Intensity ratio between $I_{\omega 1}$ and $I_{\omega 2}$
$I_{\omega 1}$: Raman scattering light intensity at Raman shift $\omega_1$ (left axis in the figure)
$I_{\omega 2}$: Raman scattering light intensity at Raman shift $\omega_2$ (lower axis in the figure)

Method of Calculating Significant Difference

The intensity ratio calculated by the above-mentioned equation was measured at a plurality of points of two kinds of tissues ("connective tissue vs myelinated nerves", etc. described in an upper part of the figure), and the two kinds of measurement groups were subjected to statistical analysis by a t-test to calculate a p-value.

Ex.) Analysis target: Myelinated Nerves and Fat Tissue

Calculation of intensity ratio with respect to $\omega_1$:2,850 cm$^{-1}$, $\omega_2$:2,933 cm$^{-1}$ Myelinated nerve intensity ratio measurement group:

$$I_{ratio1,myel}(=I_{\omega 1,myel}/I_{\omega 2,myel})\text{(Measurement point 1)},$$
$$I_{ratio2,myel}\text{(Measurement point 2)},$$

Fat tissue intensity ratio measurement group:

$$I_{ratio1,fat}(=I_{\omega 1,fat}/I_{\omega 2,fat})\text{(Measurement point 1)},$$
$$I_{ratio2,fat}\text{(Measurement point 2)},$$ [Math. 3]

These two intensity ratio measurement groups were subjected to a t-test to calculate a p-value.

In FIGS. 12 and 13, the p-value was plotted to points corresponding to the left axis 2,850 cm$^{-1}$ ($\omega_1$) and the lower axis 2,933 cm$^{-1}$ ($\omega_2$).

The same (intensity ratio calculation, t-test) was repeated by shifting $\omega_1$ and $\omega_2$.

Interpretation of Results

FIGS. 12 and 13 show p-values plotted to an intensity ratio of each Raman shift. In general, if p<0.05, it can be considered that there is a significant difference. Therefore, in FIGS. 12 and 13, it can be considered that there is a significant difference in a range of a white portion. In the white portion, tissue can be distinguished based on an intensity ratio. In the white portion, nerves can be specifically displayed in Steps 3 and 4. In the preferred embodiment of the present invention, an intensity ratio between 2,855 $cm^{-1}$ or a peak wave number range of around 2,855 $cm^{-1}$ and 2,933 $cm^{-1}$ or a peak wave number range of around 2,933 $cm^{-1}$, or an intensity ratio between 2,887 $cm^{-1}$ or a peak wave number range of around 2,887 $cm^{-1}$ and 2,933 $cm^{-1}$ or a peak wave number range of around 2,933 $cm^{-1}$ can be used. Herein, the "peak wave number range of around" in 2,855 $cm^{-1}$ or a peak wave number range of around 2,855 $cm^{-1}$, 2,933 $cm^{-1}$ or a peak wave number range of around 2,933 $cm^{-1}$, and 2,887 $cm^{-1}$ or a peak wave number range of around 2,887 $cm^{-1}$ means that the wave numbers of 2,855 $cm^{-1}$, 2,933 $cm^{-1}$, and 2,887 $cm^{-1}$ can be changed in the range of the white portion.

Example 3

Raman Spectrum by 671 nm Excitation

Figure 14:
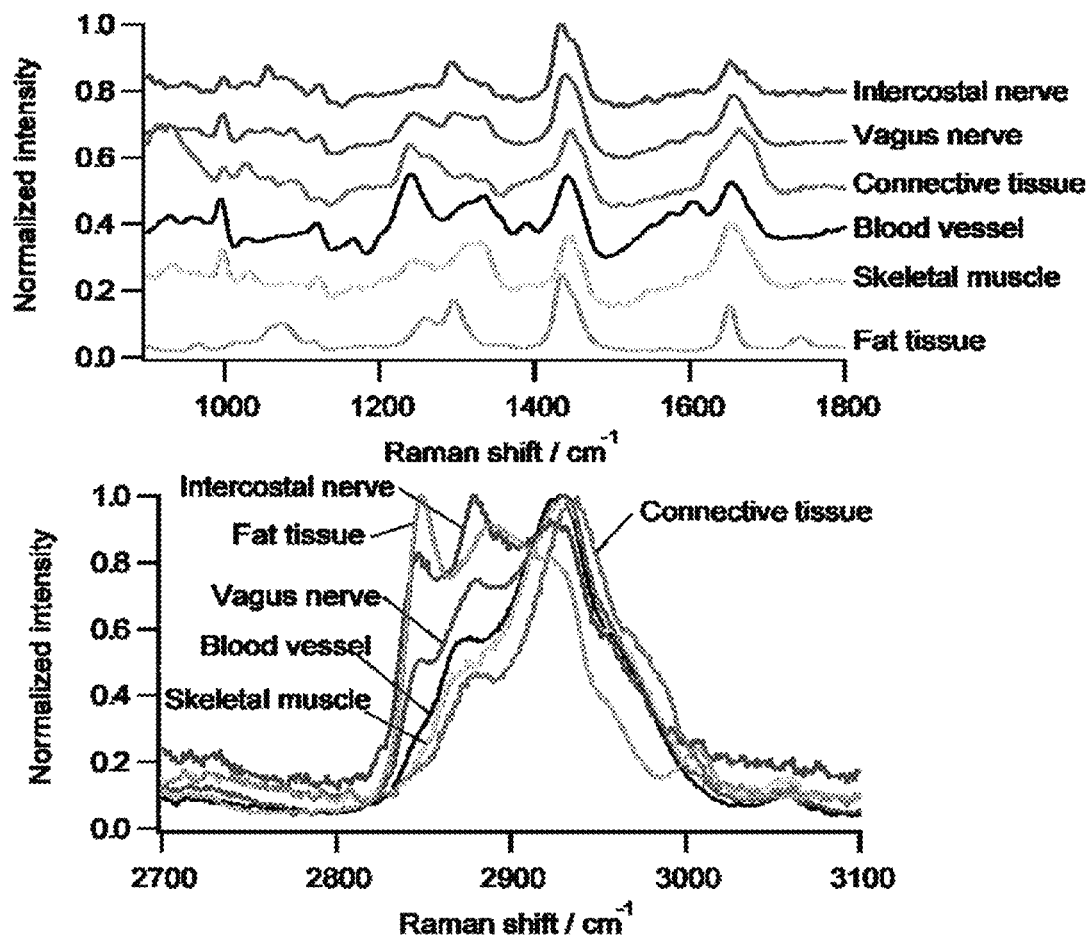
FIG. 14 shows Raman spectrum of each tissue by 671 nm excitation, corresponding to intercostal nerves (myelinated nerves), vagus nerves (unmyelinated nerves), fibrous connective tissue, blood vessels (media), skeletal muscle, and fat tissue.
Figure 15:
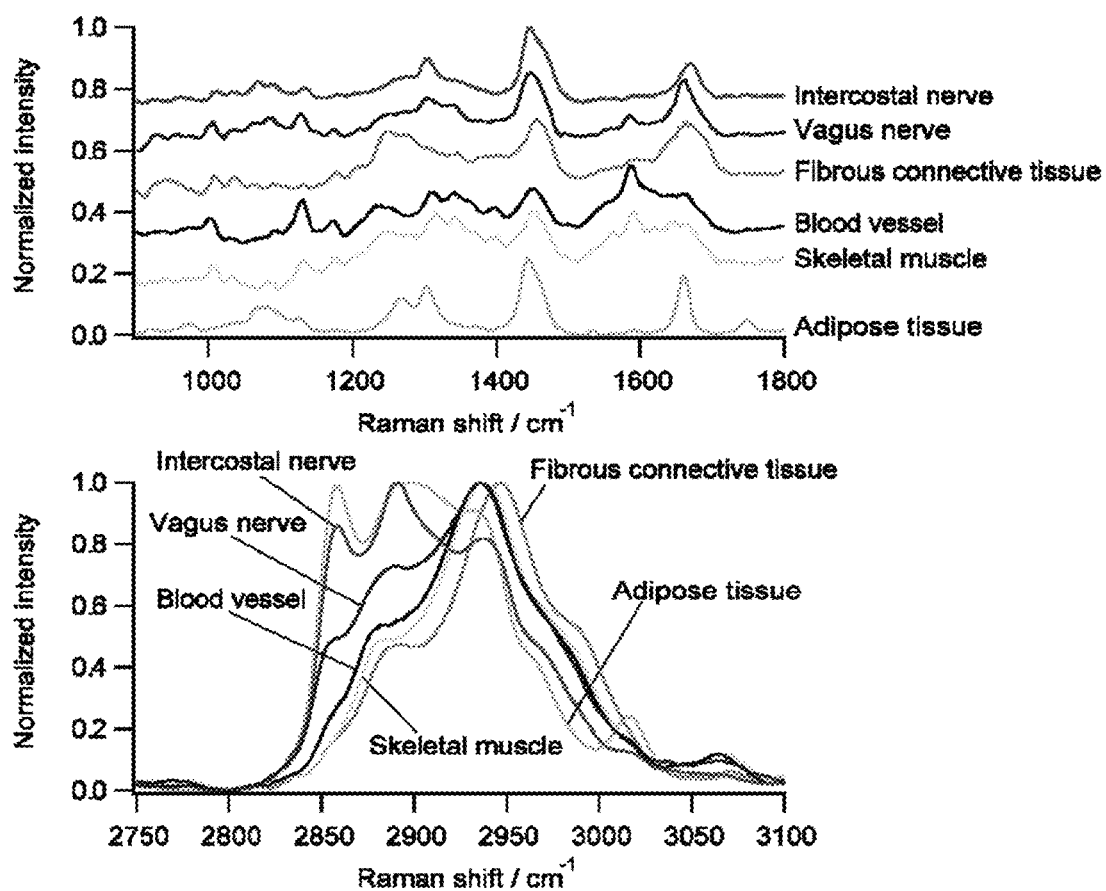
FIG. 15 shows Raman spectrum of each tissue by 532 nm excitation, corresponding to intercostal nerves (myelinated nerves), vagus nerves (unmyelinated nerves), fibrous connective tissue, blood vessels (media), skeletal muscle, and fat tissue.

In order to show that nerves can be detected at various wavelengths, a Raman spectrum at an excitation optical wavelength of 671 nm was measured (FIG. 14). For reference, FIG. 15 shows the measurement result at an excitation optical wavelength of 532 nm.

A Raman spectrum that was substantially the same as that at 532 nm was also obtained at each spectrum. From this, it is considered that nerves can be detected similarly at various wavelengths.

The invention claimed is:

1. A device for detecting nerves containing unmyelinated nerves, the device comprising:
   excitation light irradiation means for irradiating a sample with excitation light;
   means for detecting Raman scattering light from the sample;
   a spectroscopic portion for dispersing the received Raman scattering light into a spectrum component of each wavelength/wave number;
   intensity ratio calculation means for calculating an intensity ratio of a specific wavelength/specific wave number of the Raman scattering light or analyzing means for extracting a feature of the intensity ratio and subjecting the feature to multivariate analysis and/or statistical analysis; and
   means for specifically displaying (i) nerves including myelinated nerves and unmyelinated nerves, separate from other tissue, and (ii) unmyelinated nerves, separate from myelinated nerves and other tissue, using the intensity ratio as an index.

2. The device for detecting nerves according to claim 1, wherein the light source comprises a laser light source.

3. The device for detecting nerves according to claim 2, further comprising a detector for detecting a Raman spectrum.

4. The device for detecting nerves according to claim 1, further comprising a detector for detecting a Raman spectrum.

5. The device for detecting nerves according to claim 1, wherein the intensity ratio is one of an intensity ratio between 2,855 $cm^{-1}$ or a peak wave number range of around 2,855 $cm^{-1}$ and 2,933 $cm^{-1}$ or a peak wave number range of around 2,933 $cm^{-1}$ and an intensity ratio between 2,887 $cm^{-1}$ or a peak wave number range of around 2,887 $cm^{-1}$ and 2,933 $cm^{-1}$ or a peak wave number range of around 2,933 $cm^{-1}$.

6. The device for detecting nerves according to claim 5, wherein a combination of a numerator and a denominator of the intensity ratio is any one of the following items (i) to (iii):
   (i) when the numerator is 2,855 $cm^{-1}$, the denominator is any wave number within a wave number range of from 2,859 $cm^{-1}$ to 3,024 $cm^{-1}$ and 3,068 $cm^{-1}$ to 3,100 $cm^{-1}$;
   (ii) when the numerator is 2,887 $cm^{-1}$, the denominator is any wave number within a wave number range of from 2,899 $cm^{-1}$ to 3,024 $cm^{-1}$; and
   (iii) when the numerator is 2,933 $cm^{-1}$, the denominator is any wave number within a wave number range of from 2,813 $cm^{-1}$ to 2,912 $cm^{-1}$, 2,940 $cm^{-1}$ to 3,021 $cm^{-1}$, and 3,073 $cm^{-1}$ to 3,089 $cm^{-1}$.

7. The device for detecting nerves according to claim 1, wherein the intensity ratio is an intensity ratio between 2,855 $cm^{-1}$ and 2,933 $cm^{-1}$ or an intensity ratio between 2,887 $cm^{-1}$ and 2,933 $cm^{-1}$.

* * * * *